(12) United States Patent
Bristol et al.

(10) Patent No.: US 10,023,650 B2
(45) Date of Patent: *Jul. 17, 2018

(54) RECOMBINANT MONOCLONAL ANTIBODIES AND CORRESPONDING ANTIGENS FOR COLON AND PANCREATIC CANCERS

(71) Applicant: PRECISION BIOLOGICS, INC., Rockville, MD (US)

(72) Inventors: J. Andrew Bristol, Rockville, MD (US); Judith A. Kantor, Glenshaw, PA (US)

(73) Assignee: PRECISION BIOLOGICS, INC., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/158,638

(22) Filed: May 19, 2016

(65) Prior Publication Data

US 2016/0326260 A1    Nov. 10, 2016

Related U.S. Application Data

(62) Division of application No. 14/308,851, filed on Jun. 19, 2014, now Pat. No. 9,371,375, which is a division of application No. 13/012,706, filed on Jan. 24, 2011, now Pat. No. 8,802,090, which is a division of application No. 12/859,526, filed on Aug. 19, 2010, now Pat. No. 8,524,456, which is a division of application No. 12/266,889, filed on Nov. 7, 2008, now Pat. No. 7,829,678.

(60) Provisional application No. 60/996,255, filed on Nov. 8, 2007.

(51) Int. Cl.
| | |
|---|---|
| C07K 16/00 | (2006.01) |
| C07K 16/30 | (2006.01) |
| A61K 39/395 | (2006.01) |
| A61K 45/06 | (2006.01) |
| C07K 16/18 | (2006.01) |
| G01N 33/574 | (2006.01) |
| A61K 47/48 | (2006.01) |
| G01N 33/577 | (2006.01) |
| A61K 39/00 | (2006.01) |

(52) U.S. Cl.
CPC .... *C07K 16/3046* (2013.01); *A61K 39/39558* (2013.01); *A61K 45/06* (2013.01); *A61K 47/486* (2013.01); *A61K 47/48615* (2013.01); *C07K 16/18* (2013.01); *C07K 16/303* (2013.01); *G01N 33/577* (2013.01); *G01N 33/57419* (2013.01); *G01N 33/57438* (2013.01); *A61K 2039/505* (2013.01); *C07K 2317/24* (2013.01); *C07K 2317/51* (2013.01); *C07K 2317/515* (2013.01); *C07K 2317/52* (2013.01); *C07K 2317/565* (2013.01); *C07K 2317/732* (2013.01)

(58) Field of Classification Search
None
See application file for complete search history.

(56) References Cited

U.S. PATENT DOCUMENTS

| | | | |
|---|---|---|---|
| 4,810,781 A | 3/1989 | Hollinshead et al. |
| 5,431,897 A | 7/1995 | Welt et al. |
| 5,530,101 A | 6/1996 | Queen et al. |
| 5,712,369 A | 1/1998 | Old et al. |
| 5,851,526 A | 12/1998 | Welt et al. |
| 6,190,640 B1 | 2/2001 | Welt et al. |
| 6,291,235 B1 | 9/2001 | Welt et al. |
| 6,307,026 B1 | 10/2001 | King et al. |
| 6,652,853 B2 | 11/2003 | Welt et al. |
| 7,125,689 B2 | 10/2006 | Carr et al. |
| RE39,760 E | 8/2007 | Tsuang et al. |
| 7,314,622 B2 | 1/2008 | Arlen et al. |
| 7,829,678 B2 | 11/2010 | Bristol et al. |
| 8,524,456 B2 | 9/2013 | Bristol et al. |
| 8,802,090 B2 | 8/2014 | Bristol et al. |
| 2001/0047083 A1 | 11/2001 | Chatterjee et al. |
| 2003/0018171 A1 | 1/2003 | Anderson et al. |
| 2003/0031671 A1 | 2/2003 | Welt et al. |
| 2003/0040027 A1 | 2/2003 | Ritter et al. |
| 2005/0191617 A1 | 9/2005 | Inoue et al. |
| 2007/0020273 A1 | 1/2007 | Arlen et al. |
| 2007/0031327 A1 | 2/2007 | Luzzi et al. |
| 2009/0041783 A1 | 2/2009 | Takayama et al. |

FOREIGN PATENT DOCUMENTS

| | | |
|---|---|---|
| AU | 2007351514 | 10/2008 |
| MX | 301576 | 7/2012 |
| WO | 2007/008712 | 1/2007 |
| WO | 2008/127271 | 10/2008 |
| WO | 2009/062050 | 5/2009 |
| WO | 2011/163401 | 12/2011 |

(Continued)

OTHER PUBLICATIONS

Blumenthal et al., (2005) Cancer Immunology Immunotherapy 54(4): 315-327.
Blumenthal et al., (2007) BMC Cancer 7:2.
Burgess et al., (1990) "Possible dissociation of the heparin-binding ant mitogenic activities of heparin-binding (acidic fibroblast) growth factor 1 from its receptor binding activities by site-directed mutagenesis of a single lysine residue", Journal of Cell Biology 111:2129-2138.
Casset et al., (2003) "A peptide mimetic of an anti-CD4 monoclonal antibody by rational design", Biochemical and Biophysical Research Communications 307:198-205.
Chen et al., (1999) "Selection and analysis of an optimized anti-VEGF antibody: crystal structure of an affinity-matured Fab in complex with antigen", Journal of Molecular Biology 293:865-881.

(Continued)

*Primary Examiner* — Sean E Aeder
(74) *Attorney, Agent, or Firm* — Robin L. Teskin; LeClairRyan PLLC

(57) ABSTRACT

The present invention provides for recombinant monoclonal antibodies that bind to human colorectal and pancreatic carcinoma-associated antigens, along with nucleic acid sequences encoding the antibody chains, and the amino acid sequences corresponding to the nucleic acids, and uses for these antibodies, nucleic acids and amino acids.

20 Claims, 8 Drawing Sheets

(56) References Cited

FOREIGN PATENT DOCUMENTS

WO  2006/113546  7/2012

OTHER PUBLICATIONS

De Pascalis et al., (2002) "Grafting of 'abbreviated' complimentarity-determiining regions containing specificity-determining residues essential for ligand contact to engineer a less immunogenic humanized monoclonal antibody", Journal of Immunology 169: 3076-3084.

Heath et al., (1997) "The human A33 antigen is a transmembrane glycoprotein and a novel member of the immunoglobulin superflamily", Proc. Natl. Acad. Sci. USA 94(2): 469-474.

Herlyn et al., (1982) "Monoclonal Antibody Detection of a Circulating Tumor-Associated Antigen. I. Presence of antigen in sera of patients with colorectal, gastric, and pancreatic carcinoma", J. Clin. Immunol. 2(2): 135-140.

Hollinshead et al., (1970) "Skin-reactive soluble antigen from intestinal cancer-cell-membranes and relationship to carcinoembryonic antigens", Lancet 1(7658): 1191-1195.

Hollinshead et al., (1972) "Separation of skin reactive intestinal cancer antigen from the carcinoembryonic antigen of Gold", Science 177(52):887-889.

Hollinshead et al., (1973) "Further comparisons of separated intestinal cancer, fetal intestinal and normal intestinal soluble membrane antigen and the role of tumor related antigens in the diagnosis and treatment of intestinal cancer", Proc. Second. Intl. Symp. Cancer Detection and Prevention. Bologna, Italy, pp. 616-620.

Hollinshead et al., (1985) "Specific active immunotherapy in patients with adenocarcinoma of the colon utilizing tumor-associated antigens (TAA). A phase I clinical trial", Cancer 56: 480-489.

Holm et al., (2007) "Functional mapping and single chain construction of the anti-cytokeratin 8 monoclonal antibody TS1", Molecular Immunology 44: 1075-1084.

International Search Report dated Aug. 22, 2008.

Johnstone et al., (2000) "Characterization of mouse A33 antigen, a definitive marker for basolateral surfaces of intestinal epithelial cells", Am. J. Physiol. Gastrointest. Liver Physiol. 2000 279(3): Ci500-Ci510.

Kurihara et al., (1979) "Soluble membrane antigens of gastric cancer cells: an analysis and study of activity in inducing cell-mediated immune responses", J. Jap. Soc. Cancer Ther. 14(3): 313-324.

Lazar et al., (1988) "Transforming growth factor a: mutation of aspartic acid 47 and leucine 48 results in different biological activities", Molecular and Cellular Biology 8: 1247-1252.

Mac Callum et al., (1996) "Antibody-antigen interactions: contact analysis and binding site topography", Journal of Molecular Biology 262: 732-745.

Ritter et al., (1997) "Characterization of posttranslational modifications of human A33 antigen, a novel palitoylated surface glycoprotein of human gstrointestinal epithelium", Biochem. Biophys. Res. Commun. 236(3): 682-686.

Ritter et al., (2001) "Serological analysis of human anti-human antibody responses in colon cancer patients treated with repeated doses of humanized monoclonal antibody A33", Cancer Res. 61:6851-6859.

Rudikoff et al., (1982) "Single amino acid substitution altering antigen binding specificity", Proceedings of the National Academy of Sciences 79: 1979-1983.

Sears et al., (1982) "Monoclonal Antibody Detection of a Circulating Tumor-Associated Antigen. II. A Longitudinal Evaluation of Patients with Colorectal Cancer", Journal of Clinical Immunology 2:2.

Strickland et al., (2009) The Journal of Pathology 218(3): 380-390.

Vafa et al., Journal of Clinical Oncology 2006 ASCO Annual Meeting Proceedings Part I, vol. 24, No. 18S (Jun. 20 Supplement), 2006: 12506.

Vajdos et al., (2002) "Comprehensive functional maps of the antigen-binding site of an anti-ErbB2 antibody obtained with shotgun scanning mutagenesis", Journal of Molecular Biology 320: 415-428.

Welt, S. (2003) "Phase I study of anticolon cancer humanized antibody A33", Clin. Cancer Res. 9:1338-1346.

Wu et al., (1999) "Humanization of a murine monoclonal antibody by simultaneous optimization of framework and CDR residues", Journal of Molecular Biology 294:151-162.

Rittenhouse HG, Manderino GL, Hass GM. Mucin-type glycoproteins as tumor markers. Laboratory Medicine. Sep. 1, 1985;16(9):556-60.

Bristol et al. "Pre-clinical development of a novel therapeutic antibody to treat pancreas and colorectal cancers", Human Antibo, IOS Press, Amsterdam, NL, vol. 19, No. 2-3, Jan. 1, 2010 (Jan. 1, 2010), pp. 36-37.

Luka J, Arlen PM, Bristol A. Development of a serum biomarker assay that differentiates tumor-associated MUC5AC (NPC-1C Antigen) from normal MUC5AC. BioMed Research International. Dec. 16, 2010;2011.

The 16C3 hybridoma Kappa light chain DNA, full-length sequence:

GCGGGGCAGCCTCACACAGAACACACACAGATATGGGTGTACCCACTCAGCT
CCTGTTGCTGTGGCTTACAGTCGTAGTTGTCAGATGTGACATCCAGATGACTC
AGTCTCCAGCTTCACTGTCTGCATCTGTGGGAGAAACTGTCACCATCACATGT
GGAGCAAGTGAGAATATTTACGGTGCTTTAAATTGGTATCAGCGGAAACAGG
GAAAATCTCCTCAGCTCCTGATTTATGGCGCAAGTAATTTGGCAGATGGCATG
TCATCGAGGTTCAGTGGCAGTGGATCTGGTAGACAGTATTCTCTCAAGATCA
GTAGCCTGCATCCTGACGATGTTGCAACGTATTACTGTCAAAATGTATTAAGT
AGTCCGTACACGTTCGGAGGGGGGACCAAGCTGGAAATAAAACGGGCTGAT
GCTGCACCAACTGTATCCATCTTCCCACCATCCAGTGAGCAGTTAACATCTGG
AGGTGCCTCAGTCGTGTGCTTCTTGAACAACTTCTACCCCAAAGACATCAATG
TCAAGTGGAAGATTGATGGCAGTGAACGACAAAATGGCGTCCTGAACAGTTG
GACTGATCAGGACAGCAAAGACAGCACCTACAGCATGAGCAGCACCCTCAC
GTTGACCAAGGACGAGTATGAACGACATAACAGCTATACCTGTGAGGCCACT
CACAAGACACCAACTTCACCCATTGTCAAGAGCTTCAACAGGAATGAGTGT
*TAG*AGACAAAGGTCCTGAGACGCCACCACCAGCTCCCCAGCTCCATCCTATC
TTCCCTTCTAAGGTCTTGGAGGCTTCCCCACAAGCGACCTACCACTGTTGCGG
TGCTCCAAACCTCCTCCCCACCTCCTTCTCCTCCTCCTCCCTTTCCTTGGCTTTT
ATCATGCTAATATTTGCAGAAAATATTCAATAAAGTGAGTCTTTGCACAAAA
AAAAAAAAAAAAAAAAAAAAAA (SEQ ID NO:12)

FIG. 2

The 16C3 hybridoma IgG heavy chain DNA, full-length sequence:

ACGCGGGACACAGTAGTCTCTACAGTCACAGGAGTACACAGGACATTGCC
ATGGGTTGGAGCTGTATCATCTTCTTTCTGGTAGCAACAGCTACAGGTGTGCA
CTCCCAGGTCCAGCTGCAGCAGTCTGGGCCTGAGGTGGTGAGGCCTGGGGTC
TCAGTGAAGATTTCCTGCAAGGGTTCCGGCTACACATTCACTGATTATGCTAT
GCACTGGGTGAAGCAGAGTCATGCAAAGAGTCTCGAGTGGATTGGACTTATT
AGTACTTACAGTGGTGATACAAAGTACAACCAGAACTTTAAGGGCAAGGCCA
CAATGACTGTAGACAAATCCTCCAACACAGCCTATATGGAACTTGCCAGATT
GACATCTGAGGATTCTGCCATCTATTACTGTGCAAGAGGGGATTATTCCGGTA
GTAGGTACTGGTTTGCTTACTGGGGCCAAGGGACTCTGGTCACTGTCTCTGCA
GCCAAAACGACACCCCATCTGTCTATCCACTGGCCCTGGATCTGCTGCCCA
AACTAACTCCATGGTGACCCTGGGATGCCTGGTCAAGGGCTATTTCCCTGAGC
CAGTGACAGTGACCTGGAACTCTGGATCCCTGTCCAGCGGTGTGCACACCTT
CCCAGCTGTCCTGCAGTCTGACCTCTACACTCTGAGCAGCTCAGTGACTGTCC
CCTCCAGCACCTGGCCCAGCGAGACCGTCACCTGCAACGTTGCCCACCCGGC
CAGCAGCACCAAGGTGGACAAGAAAATTGTGCCCAGGGATTGTGGTTGTAAG
CCTTGCATATGTACAGTCCCAGAAGTATCATCTGTCTTCATCTTCCCCCCAAA
GCCCAAGGATGTGCTCACCATTACTCTGACTCCTAAGGTCACGTGTGTTGTGG
TAGACATCAGCAAGGATGATCCCGAGGTCCAGTTCAGCTGGTTTGTAGATGA
TGTGGAGGTGCACACAGCTCAGACGCAACCCCGGGAGGAGCAGTTCAACAG
CACTTTCCGCTCAGTCAGTGAACTTCCCATCATGCACCAGGACTGGCTCAATG
GCAAGGAGTTCAAATGCAGGGTCAACAGTGCAGCTTTCCCTGCCCCCATCGA
GAAAACCATCTCCAAAACCAAAGGCAGACCGAAGGCTCCACAGGTGTACAC
CATTCCACCTCCCAAGGAGCAGATGGCCAAGGATAAAGTCAGTCTGACCTGC
ATGATAACAGACTTCTTCCCTGAAGACATTACTGTGGAGTGGCAGTGGAATG
GGCAGCCAGCGGAGAACTACAAGAACACTCAGCCCATCATGGACACAGATG
GCTCTTACTTCGTCTACAGCAAGCTCAATGTGCAGAAGAGCAACTGGGAGGC
AGGAAATACTTTCACCTGCTCTGTGTTACATGAGGGCCTGCACAACCACCATA
CTGAGAAGAGCCTCTCCCACTCTCCTGGTAAA*__TGA__*TCCCAGTGTCCTTGGAGC
CCTCTGGCCCTACAGGACTTTGACACCTACCTCCACCCCTCCCTGTATAAATA
AAGCACCCAGCACTGCCTCGGGACCCTGCATAAAAAAAAAAAAAAAAAAAAA
AAAAAAA (SEQ ID NO:13)

FIG. 3

LMTQSPASLSASVGETVTITCGASENIYGALNWYQRKQGKSPQLLIYGASNLAD
GMSSRFSGSGSGRQYSLKISSLHPDDVATYYCQNVLSSPYTFGGGTKLEIKKG
(SEQ ID NO:14)

FIG. 4

LEESGPEVVRPGVSVKISCKGSGYTFTDYAMHWVKQSHAKSLEWIG**LISTYSGD
TKYNQNFKGKATMTVDKSSNTAYMELARLTSEDSAIYYCARGDYSGSRYWFA
Y**WGQGTTVTR (SEQ ID NO:15)

```
                 10         20      27abcdef  30         35         40         49
                  |          |          |      |          |          |          |
16C3      DIQMTQSPASLSASVGETVTITC  GASE------NIYGALN  WYQRKQGKSPQLLIY
ven16C3   DIQMTQSPSSLSASVGDRVTITC  GASE------NIYGALN  WYQRKPGKSPKLLIY
cdr16C3   DIQMTQSPSSLSASVGDRVTITC  GASE------NIYGALN  WYQRKPGKSPKLLIY
abb16C3   DIQMTQSPSSLSASVGDRVTITC  QASE------NIYGALN  WYQRKPGKSPKLLIY
sdr16C3   DIQMTQSPSSLSASVGDRVTITC  QASE------NIYGALN  WYQRKPGKSPKLLIY
fra16C3   DIQMTQSPSSLSASVGDRVTITC  GASE------NIYGALN  WYQRKPGKSPNLLIY 60         70         80         88         95ab
                      |          |          |          |          |
16C3      GASNLAD  GMSSRFSGSGSGRQYSLKISSLHPDDVATYYC  QNVLSSP--YT
ven16C3   GASNLAD  GMPSRFSGSGSGRQYTLTISSLQPEDVATYYC  QNVLSSP--YT
cdr16C3   GASNLAD  GMPSRFSGSGSGRQYTLTISSLQPEDVATYYC  QNVLSSP--YT
abb16C3   GASNLAT  GMPSRFSGSGSGTDYTFTISSLQPEDIATYYC  QNVLSSP--YT
sdr16C3   GASNLAT  GMPSRFSGSGSGRQYTFTISSLQPEDIATYYC  QQVLSSP--YT
fra16C3   GASNLAD  GMPSRFSGSGSGRQYTLTISSLQPEDVATYYC  QNVLSSP--YT 98        107
                   |          |
16C3      FGGGTKLEIK (SEQ ID NO:16)
ven16C3   FGGGTKLEIK (SEQ ID NO:17)
cdr16C3   FGGGTKLEIK (SEQ ID NO:18)
abb16C3   FGGGTKLEIK (SEQ ID NO:19)
sdr16C3   FGGGTKLEIK (SEQ ID NO:20)
fra16C3   FGGGTKLEIK (SEQ ID NO:21)
```

```
                10         20         30 ab    35        40        49
                 |          |          |  |     |         |         |
16C3       QVQLQQSGPEVVRPGVSVKISCKGSGYTFT --DYAMH WVKQSHAKSLEWIG
ven16C3    QVQLVQSGAEVKKPGASVKVSCKGSGYTFT --DYAMH WVRQAPGQRLEWIG
cdr16C3    QVQLVQSGAEVKKPGASVKVSCKGSGYTFT --DYAMH WVRQAPGQGLEWIG
abb16C3    QVQLVQSGAEVKKPGASVKVSCKASGYTFT --DYAMH WVRQAPGQRLEWMG
sdr16C3    QVQLVQSGAEVKKPGASVKVSCKASGYTFT --DYAMH WVRQAPGQRLEWIG
fra16C3    QVQLVQSGAEVKKPGASVKVSCKGSGYTFT --DYAMH WVRQVHAQGLEWIG 52abc      60        66   70              82abc       90   94
             |         |         |    |                 |          |   |
16C3       LIST--YSGDTKYNQNFKG KATMTVDKSSNTAYMELARLTSEDSAIYYCAR
ven16C3    LIST--YSGDTKYNQNFKG KATMTVDKSASTAYMELSSLRSEDTAVYYCAR
cdr16C3    LIST--YSGDTKYNQNFKG KATMTVDTSISTAYMELSRLRSDDTAIYYCAR
abb16C3    LIST--YSGDTKYSQKFQG RVTMTVDKSASTAYMELSSLRSEDTAVYYCAR
sdr16C3    LIST--YSGDTKYNQKFQG KATMTVDKSASTAYMELSSLRSEDTAVYYCAR
fra16C3    LIST--YSGDTKYNQNFKG KATMTVDKSTSTAYMELSSLRSEDTAVYYCAR 100abcdefghij 103        113
                |          |          |
16C3       GDYSGSRYWF------AY WGQGTLVTVSA (SEQ ID NO:22)
ven16C3    GDYSGSRYWF------AY WGQGTLVTVSS (SEQ ID NO:23)
cdr16C3    GDYSGSRYWF------AY WGQGTLVTVSS (SEQ ID NO:24)
abb16C3    GDYSGSRYWF------AY WGQGTLVTVSS (SEQ ID NO:25)
sdr16C3    GDYSGSRYWF------AY WGQGTLVTVSS (SEQ ID NO:26)
fra16C3    GDYSGSRYWF------AY WGQGTLVTVSS (SEQ ID NO:27)
```

FIG. 7

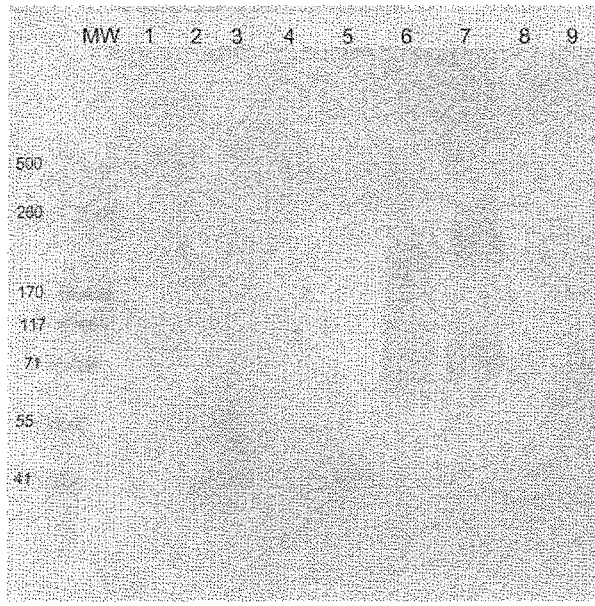

FIG. 11

H16C3-Abb* Heavy Chain:

MGWSCIIFFLVATATGVHS/QVQLVQSGAEVKKPGASVKVSCKAS**GYTFTDYA
MHWVRQAPGQRLEWMGLISTYSGDTKYNQNFQG**RVTMTVDKSASTAYMELS
SLRSEDTAVYYCARGDYSGSRYWFAYWGQGTLVTVSS/ASTKGPSVFPLAPSSK
STSGGTAALGCLVKDYFPEPVTVSWNSGALTSGVHTFPAVLQSSGLYSLSSVVTV
PSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYN
STYRVVSVLTVLHQDWLNGKEYKCKVSNKALPAPIEKTISKAKGQPREPQVYTL
PPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGK (SEQ ID NO:28)

H16C3-Abb* Light Chain:

MGVPTQLLLLWLTVVVVRC/DIQMTQSPSSLSASVGDRVTITCQASENIYGALN
WYQRKPGKSPKLLIYGASNLATGMPSRFSGSGSGTDYTFTISSLQPEDIATYYC
QQVLSSPYTFGGGTKLEIKR/TVAAPSVFIFPPSDEQLKSGTASVVCLLNNFYPRE
AKVQWKVDNALQSGNSQESVTEQDSKDSTYSLSSTLTLSKADYEKHKVYACEV
THQGLSSPVTKSFNRGEC (SEQ ID NO:29)

FIG. 12

RECOMBINANT MONOCLONAL ANTIBODIES AND CORRESPONDING ANTIGENS FOR COLON AND PANCREATIC CANCERS

CROSS-REFERENCE TO RELATED APPLICATIONS

This application is a divisional patent application of U.S. application Ser. No. 14/308,851, filed Jun. 19, 2014, which is a divisional patent application of U.S. patent application Ser. No. 13/012,706, filed Jan. 24, 2011, now U.S. Pat. No. 8,802,090, which is a divisional patent application of U.S. patent application Ser. No. 12/859,526, filed Aug. 19, 2010, now U.S. Pat. No. 8,524,456, which is a divisional patent application of U.S. patent application Ser. No. 12/266,889, filed Nov. 7, 2008, now U.S. Pat. No. 7,829,678, which claims the benefit of U.S. Provisional Application No. 60/996,255, filed Nov. 8, 2007, each of which is incorporated herein by reference.

SEQUENCE LISTING DISCLOSURE

This application includes as part of its disclosure a biological sequence listing text file named "43282o1806.txt" which was created May 18, 2016, and has a size of 28,492 bytes, which is hereby incorporated by reference in its entirety.

FIELD OF THE INVENTION

The present invention relates to the field of recombinant monoclonal antibodies and peptides and their uses in clinical and scientific procedures, including diagnostic procedures, especially where such processes involve the detection of human colorectal and pancreatic carcinoma-associated antigens (CPAA), and the characterization of the epitopes recognized by said recombinant monoclonal antibodies and peptides. The present invention also provides anti-CPAA antibodies and peptides in the form of diagnostic compounds and/or pharmaceutical compositions, useful for the diagnostic and/or therapeutic methods of the present invention for diagnosing and/or treating colorectal and pancreatic carcinoma-associated pathologies.

BACKGROUND OF THE INVENTION

According to the most recent data from the World Health Organization, from a total of fifty-eight million deaths worldwide, cancer accounted for thirteen percent of all deaths. Deaths from cancer in the world are projected to rise, with an estimated nine million people dying from cancer in the year 2015 and over eleven million dying in the year 2030. Of all cancers, colorectal cancer is the third leading cause of cancer-related deaths in the U.S., while pancreatic cancer is the eleventh most common cancer and the fourth leading cause of cancer death in both men and women. This grim scenario shows the great need for new cancer diagnostics and therapies.

Modern technology, such as that involving the use of hybridomas, has made available to researchers and clinicians sources of highly specific and potent monoclonal antibodies useful in general diagnostic and clinical procedures. For example, there are now therapeutic antibodies approved by the FDA for the treatment of colorectal cancer, such as AVASTIN® (bevacizumab, Genentech, Inc.), ERBITUX® (cetuximab injection, ImClone Sys. Inc./Merck/Bristol-Myers Squibb), and VECTIBIX® (panitumumab, Amgen Inc.).

Yet the most important challenge in fighting cancer remains the pursuit of early diagnosis. The more advanced a cancer is when diagnosed, the less likely it is that therapy will be effective. The American Cancer Society estimates that ninety percent of Americans diagnosed with stage 1 colon cancer are still alive five years after diagnosis, but only sixty-eight percent of those diagnosed with stage 3 cancer are still alive five years after diagnosis.

Hence, despite the advances in cancer research, there remains a need, for recombinant monoclonal antibodies useful for the early diagnosis and treatment of colon and pancreatic carcinomas.

SUMMARY OF THE INVENTION

An object of the present invention provides for recombinant monoclonal antibodies, or portions of recombinant monoclonal antibodies (peptides) having specificity directed to antigens and epitopes of human colorectal and pancreatic carcinoma-associated antigens (CPAA). It is therefore an object of the present invention to provide for a recombinant monoclonal antibody or a portion thereof, such as a paratope, having specificity for CPAA proteins and peptides, such as an epitope on those proteins or peptides.

A further object of the present invention provides for oligonucleotides, such as cDNAs, whose nucleotide sequences (genes) encode part or all of the heavy and light chains of the aforementioned recombinant antibodies. Accordingly, an aspect of the present invention provides for a gene encoding the variable region of a monoclonal antibody, specifically recognizing a CPAA, especially antigenic determinants or epitopes that commonly exist in a CPAA.

A further object of the present invention provides for a recombinant vector comprising the above genes. A further object of the present invention provides for a transformant obtained using the above recombinant vector.

It is a still further object of the present invention to provide recombinant antibodies specific for CPAA, wherein said antibodies are tagged with markers, making them easily isolatable as well as affording versatility in using said antibodies for research, diagnostic, and clinical purposes. A further aspect of the invention provides for a chimeric antibody that includes the variable regions of the heavy and light chains of CPAA-specific murine antibody linked to the human immunoglobulin gamma-1 and kappa constant regions, respectively. Another object of the present invention provides for a fully humanized recombinant antibody specific for CPAA. In an aspect of this embodiment, the fully humanized recombinant antibody is optimized to reduce its immunogenicity in humans, while maintaining its functionality.

It is another object of the present invention to provide a method of using the recombinant antibodies disclosed herein for research, diagnostic, and clinical uses. Particularly, an object of the present invention provides a diagnostic tool for the early detection of cancers, perhaps in patients without symptoms of disease. Another aspect provides for an immunohistochemical tool for distinguishing between slow and aggressive pancreatic cancers.

Another object of the invention provides a method for promoting tumor regression or triggering the death of transformed cells comprising administering to a patient in need thereof an antibody, portion, fragment, peptide or derivative thereof that binds to a CPAA antigen, wherein a said antibody is administered in sufficient amounts to promote tumor regression or cell death.

Yet another object of the present invention provides for methods having utility for in vitro, in situ and/or in vivo diagnosis and/or treatment of animal cells, tissues or pathologies associated with the presence of CPAA, using anti-CPAA antibodies and/or anti-CPAA peptides. The present invention also provides anti-CPAA antibodies and peptides in the form of pharmaceutical and/or diagnostic compounds and/or compositions, useful for the diagnostic and/or therapeutic methods of the present invention for diagnosing and/or treating CPAA-related pathologies.

The present invention is also directed to an anti-CPAA chimeric or humanized antibody comprising two light chains and two heavy chains, each of the chains comprising at least part of a human constant region and at least part of a variable (V) region of non-human origin having specificity to a CPAA, said antibody binding with high affinity and/or high avidity to an inhibiting and/or neutralizing epitope of CPAA-associated cells. The invention also includes a fragment or a derivative of such an antibody, such as one or more portions of the antibody chain, such as the heavy chain constant, joining, diversity or variable regions, or the light chain constant, joining or variable regions. Example portions of the antibody are one or more of the complementarity determining regions (CDRs) of the antibody, which define the specific binding to the CPAA.

It is a further object of the invention to characterize the CPAA peptides identified by the monoclonal antibodies or portions thereof. Such antigenic peptides may be useful in generating additional antigen-binding ligands, or be used as vaccines or other immunostimulatory means.

Methods are also provided for making and using anti-CPAA antibodies and peptides for various utilities of the present invention, such as but not limited to, hybridoma, recombinant or chemical synthetic methods for producing anti-CPAA antibodies or anti-CPAA peptides according to the present invention; detecting CPAA in a solution or cell; inhibiting one or more biological activities of CPAA-bearing cells in vitro, in situ or in vivo, including killing such CPAA-bearing cells. Hence, such inhibition and killing can include treatment methods of the present invention for alleviating symptoms or pathologies involving CPAA-bearing cells, such as malignancies.

BRIEF DESCRIPTION OF THE DRAWINGS

FIG. 2 presents the DNA sequence of the 16C3 murine antibody kappa light chain. The putative ATG initiating codon is indicated in bold/underlined, and the putative TAG stop codon is indicated in italics/underlined.

FIG. 3 presents the DNA sequence of 16C3 antibody IgG heavy chain. The putative ATG initiating codon is indicated in bold/underlined, and the putative TGA stop codon is indicated in italics/underlined.

FIG. 4 depicts the amino acid sequence of the 16C3 antibody kappa light chain. CDR regions are presented in bold/underlined typeface.

FIG. 5 depicts the amino acid sequence of the 16C3 heavy chain. CDR regions are presented in bold/underlined typeface.

FIG. 6 presents several humanized 16C3 variable light chains. 16C3 is the murine antibody sequence, ven16C3 has been veneered with human framework sequences, cdr16C3 has been remodeled with human CDR amino acids, abb16C3 represents abbreviated CDR grafting, sdr16C3 represents site determining amino acid changes, and fra16C3 represents a "Frankenstein" approach to remodeling the variable region by using a combination of various "pieces" of human variable regions. Numerals reflect Kabat numbering.

FIG. 7 presents several humanized 16C3 variable heavy chains. Abbreviations are identical to those of FIG. 6.

FIG. 11 shows western blot representing the 16C3 tumor antigen expressed in various fetal tissue extracts using 16C3 antibody. Lanes: 1=fetal intestine, Fx III (Hem). 8/22/72; 2=fetal intestine, Fx II (Hem), 8/22/72; 3=fetal Gut, Fx III, 2/26/73; 4=fetal Gut, Fx II, HB 11/1/72; 5=fetal Gut, Fx III, 12/20/72; 6=fetal Intestine, Fx I, 6/24/75; 7=fetal Gut, Fx I, 12/20/72; 8=fetal Gut, Fx II, 3/1/73; 9=fetal Intestine Reg 2 and Reg 3A, 8/3/74.

FIG. 12 presents the amino acid sequences of an optimized, humanized 16C3 antibody. Underlined, bolded amino acids indicate CDRs, "/" indicates the leader peptide/mature N-terminus junction and the variable/constant domain junction.

DETAILED DESCRIPTION OF THE INVENTION

Figure 1:
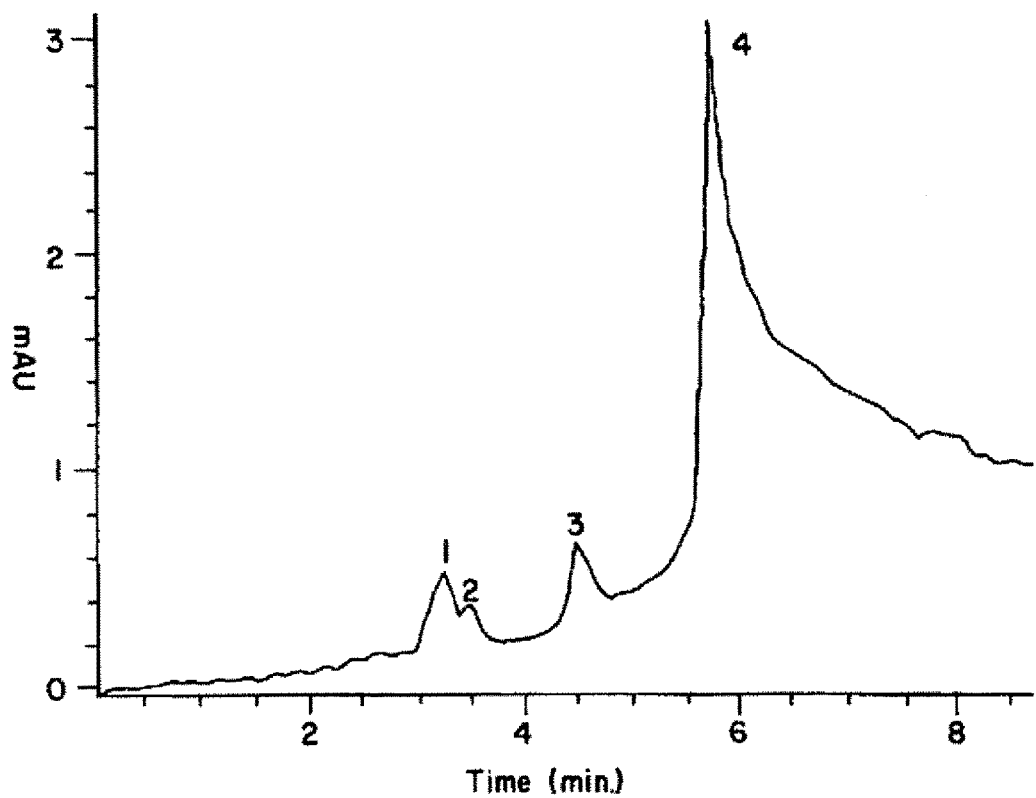
FIG. 1 is a tracing showing an HPLC elution profile of the Hollinshead "vaccine," a purified preparation of colorectal and pancreatic carcinoma cell membranes.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Unless otherwise defined, scientific and technical terms used in connection with the antibodies described herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. MOLECULAR CLONING: LAB. MANUAL (3rd ed., Cold Spring Harbor Lab. Press, Cold Spring Harbor, N.Y., 2001). The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

The present invention provides for recombinant monoclonal antibodies and peptides and their uses in clinical and scientific procedures, including diagnostic procedures, especially where such processes involve the detection of human colorectal and pancreatic carcinoma-associated antigens (CPAA), and the characterization of the epitopes recognized by said recombinant monoclonal antibodies and peptides. The present invention also provides anti-CPAA antibodies and peptides in the form of diagnostic compounds and/or pharmaceutical compositions, useful for the diagnostic and/or therapeutic methods of the present invention for diagnosing and/or treating colorectal and pancreatic carcinoma-associated pathologies. One such anti-CPAA monoclonal antibody has been characterized previously, see U.S. Pat. No. 7,314,622. The antigen-binding proteins described herein are novel, however.

Generally, monoclonal antibodies are used as invaluable reagents in diagnostics. In fact, due to their high specificities, they have played a major role in deciphering the functions of various bio-molecules in cryptic biosynthetic pathways. These have also become the reagents of choice for identification and characterization of tumor specific antigens and have become a valuable tool in the classification of cancer.

With the advent of methods of molecular biology and recombinant technology, it is possible to produce antibody and antibody-like molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with assembly of the synthesized chains to form active tetrameric ($H_2 L_2$) structures with affinity for specific epitopes and antigenic determinants. This has permitted the ready production of antibodies having sequences characteristic of neutralizing antibodies from different species and sources.

Regardless of the source of the antibodies, or how they are recombinantly constructed, or how they are synthesized, in vitro or in vivo, using transgenic animals, large cell cultures of laboratory or commercial size, using transgenic plants, or by direct chemical synthesis employing no living organisms at any stage of the process, all antibodies have a similar overall 3 dimensional structure. This structure is often given as $H_2 L_2$ and refers to the fact that antibodies commonly comprise two light (L) amino acid chains and 2 heavy (H) amino acid chains. Both chains have regions capable of interacting with a structurally complementary antigenic target. The regions interacting with the target are referred to as "variable" or "V" regions and are characterized by differences in amino acid sequence from antibodies of different antigenic specificity. The variable regions of either H or L chains contain the amino acid sequences capable of specifically binding to antigenic targets.

As used herein, the term "antigen binding region" refers to that portion of an antibody molecule which contains the amino acid residues that interact with an antigen and confer on the antibody its specificity and affinity for the antigen. The antibody region includes the "framework" amino acid residues necessary to maintain the proper conformation of the antigen-binding residues.

Within the variable regions of the H or L chains that provide for the antigen binding regions are smaller sequences dubbed "hypervariable" because of their extreme variability between antibodies of differing specificity. Such hypervariable regions are also referred to as "complementarity determining regions" or "CDR" regions. These CDR regions account for the basic specificity of the antibody for a particular antigenic determinant structure.

The CDRs represent non-contiguous stretches of amino acids within the variable regions but, regardless of species, the positional locations of these critical amino acid sequences within the variable heavy and light chain regions have been found to have similar locations within the amino acid sequences of the variable chains. The variable heavy and light chains of all antibodies each have three CDR regions, each non-contiguous with the others (termed L1, L2, L3, H1, H2, H3) for the respective light (L) and heavy (H) chains. The accepted CDR regions have been described by Kabat et al., 252 J. Biol. Chem. 6609 (1977), and CDR loops may be identified by applying these rules during an examination of a linear amino acid sequence. The rules for defining the CDR-H3 loop can vary, however (see Chapter 4, ANTIBODY ENGIN. METHODS & PROTOCOLS, (Lo, ed. Humana Press, Totowa, N.J., 2004)), and the actual boundaries of some CDR-H3 loops may not be identified without experimental techniques such as circular dichroism, nuclear magnetic resonance, or X-ray crystallography.

In all mammalian species, antibody peptides contain constant (i.e., highly conserved) and variable regions, and, within the latter, there are the CDRs and the so-called "framework regions" made up of amino acid sequences within the variable region of the heavy or light chain but outside the CDRs.

Regarding the antigenic determinate recognized by the CDR regions of the antibody, this is also referred to as the "epitope." In other words, epitope refers to that portion of any molecule capable of being recognized by, and bound by, an antibody (the corresponding antibody binding region may be referred to as a paratope). In general, epitopes consist of chemically active surface groupings of molecules, for example, amino acids or sugar side chains, and have specific three-dimensional structural characteristics as well as specific charge characteristics.

An "antigen" is a molecule or a portion of a molecule capable of being bound by an antibody which is additionally capable of inducing an animal to produce an antibody capable of binding to an epitope of that antigen. An antigen may have one or more than one epitope. The specific reaction referred to above is meant to indicate that the antigen will react, in a highly selective manner, with its corresponding antibody and not with the multitude of other antibodies which may be evoked by other antigens.

Thus, the term "antibody" is meant to include both intact immunoglobulin molecules as well as portions, fragments, peptides and derivatives thereof, such as, for example, Fab, Fab', F(ab')$_2$, Fv, Fsc, CDR regions, paratopes, or any portion or peptide sequence of the antibody that is capable of binding an antigen or epitope. An antibody is said to be "capable of binding" a molecule if it is capable of specifically reacting with the molecule to thereby bind the molecule to the antibody.

Antibody also includes chimeric antibodies, humanized antibodies, anti-idiotypic (anti-Id) antibodies to antibodies that can be labeled in soluble or bound form, as well as fragments, portions, regions, peptides or derivatives thereof, provided by any known technique, such as, but not limited to, enzymatic cleavage, peptide synthesis, or recombinant techniques. Such antibodies of the present invention are capable of binding portions of CPAA or CPAA-bearing cells. Antibody fragments or portions may lack the Fc fragment of intact antibody, clear more rapidly from the circulation, and may have less non-specific tissue binding than an intact antibody. Examples of antibody fragments may be produced from intact antibodies using methods well known in the art, for example by proteolytic cleavage with enzymes such as papain (to produce Fab fragments) or pepsin (to produce F(ab')$_2$ fragments). See, e.g., Wahl et al., 24 J. Nucl. Med. 316 (1983). Portions of antibodies may be made by any of the above methods, or may be made by expressing a portion of the recombinant molecule. For example, the CDR region(s) of a recombinant antibody may be isolated and subcloned into the appropriate expression vector. See, e.g., U.S. Pat. No. 6,680,053.

Clone 16C3 Oligonucleotide and Amino Acid Sequences

The present invention provides for a novel monoclonal antibody that specifically binds a CPAA. This monoclonal antibody, identified as "16C3", which refers to the number assigned to its hybridoma clone. Herein, 16C3 also refers to the portion of the monoclonal antibody, the paratope or CDRs, that bind specifically with a CPAA epitope identified as 16C3 because of its ability to bind the 16C3 antibody. The several recombinant and humanized forms of 16C3 described herein may be referred to by the same name.

The present invention includes, within its scope, DNA sequences encoding the variable regions of the light and heavy chains of the anti-CPAA antibody of the present invention. A nucleic acid sequence encoding the variable region of the light chain of the 16C3 antibody is presented in FIG. 2. A nucleic acid sequence encoding the variable region of the heavy chain of the 16C3 antibody is presented in FIG. 3.

The present invention includes, within its scope, a peptide of the 16C3 light chain comprising the amino acid sequence depicted in FIG. 4 and FIG. 12; and a peptide of the 16C3 heavy chain comprising the amino acid sequence depicted in FIG. 5 and FIG. 12. Further, the present invention includes the CDR regions depicted for the 16C3 kappa light chain which are the residues underlined in FIG. 4, having the amino acids of CDR 1: GASENIYGALN (SEQ ID NO:1); CDR 2: GASNLAD (SEQ ID NO:2); and CDR 3: QNVLSSPYT (SEQ ID NO:3); as well as the amino acids the light chain underlined in FIG. 12, which include CDR 1: QASENIYGALN (SEQ ID NO:4); CDR 2: GASNLAT (SEQ ID NO:5); and CDR 3: QQVLSSPYT (SEQ ID NO:6). The invention similarly identifies the CDR regions for the heavy chain, underlined in FIG. 5, which include the amino acids for CDR 1: GYTFTDYAMH (SEQ ID NO:7); CDR 2: LISTYSGDTKYNQNFKG (SEQ ID NO: S); and CDR 3: CDYSGSRYWFAY (SEQ ID NO:9); as well as the amino acids the heavy chain underlined in FIG. 12, which include CDR 1: GYTFTDYAMH (SEQ ID NO:7); CDR 2: ISTYSGDTKYNQNFQG (SEQ ID NO:10); and CDR 3: GDYSGSRYWFAY (SEQ ID NO:11).

Included also within the scope of the invention is any oligonucleotide sequence that encodes the amino acid sequence of 16C3 or a peptide thereof. Because the genetic code is degenerate, more than one codon can be used to encode a particular amino acid. Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic or prokaryotic cells expressing an anti-CPAA antibody or portion. Such "codon usage rules" are disclosed by Lathe, et al., 183 J. Molec. Biol. 1 (1985). Using the "codon usage rules" of Lathe, a single oligonucleotide, or a set of oligonucleotides, that contains a theoretical "most probable" nucleotide sequence capable of encoding anti-CPAA sequences is identified.

Although occasionally an amino acid sequence can be encoded by only a single oligonucleotide, frequently the amino acid sequence can be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the protein.

The oligonucleotide, or set of oligonucleotides, containing the theoretical "most probable" sequence capable of encoding an anti-CPAA antibody or peptide including a variable or constant region is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the variable or constant region anti-CPAA gene (Sambrook et al., 1989).

A suitable oligonucleotide, or set of oligonucleotides, which is capable of encoding a peptide of 16C3 (or which is complementary to such an oligonucleotide, or set of oligonucleotides) is identified (using the above-described procedure), synthesized, and hybridized by means well known in the art, against a DNA or a cDNA preparation derived from cells which are capable of expressing anti-CPAA antibodies or variable or constant regions thereof. Single stranded oligonucleotide molecules complementary to the "most probable" anti-CPAA region peptide coding sequences can be synthesized using procedures which are well known to those of ordinary skill in the art. See Belagaje et al., 254 J. Biol. Chem. 5765 (1979); Maniatis et al., in MOLEC. MECH. IN CONTROL OF GENE EXPRESSION (Nierlich et al., eds., Acad. Press, N Y, 1976); Wu et al., 1978; Khorana, 203 Science 614 (1979).

Additionally, DNA synthesis can be achieved through the use of automated synthesizers. Techniques of nucleic acid hybridization are disclosed by Sambrook et al., 1989, and by Haymes et al., in NUCLEIC ACID HYBRIDIZATION, A PRACTICAL APPROACH (IRL Press, DC 1985). Hybridization wash conditions can include wash solution of 0.2×SSC/0.1% SDS and incubation with rotation for 10 minutes at room temperature, (low stringency wash), wash solution of prewarmed (42° C.) 0.2×SSC/0.1% SDS and incubation with rotation for fifteen minutes at 42° C. (medium stringency wash) and wash solution of prewarmed (68° C.) 0.1×SSC/0.1% SDS and incubation with rotation for fifteen minutes at 68° C. (high stringency wash). See Ausubel et al., ANTIBODIES: A LAB. MANUAL, (Harlow & Lane eds., Cold Spring Harbor Lab., 1988). Techniques such as, or similar to, those described above have successfully enabled the cloning of genes for human aldehyde dehydrogenases (Hsu et al., 82 PNAS 3771 (1985)), fibronectin (Suzuki et al., 4 Bur. Mol. Biol. Organ. J. 2519 (1985)), the human estrogen receptor gene (Walter et al., 82 PNAS 7889 (1985)), tissue-type plasminogen activator (Pennica et al., 301 Nature 214 (1983)) and human term placental alkaline phosphatase complementary DNA (Keun et al., 82 PNAS 8715 (1985)).

It is also intended that the antibody coding regions for use in the present invention could also be provided by altering existing antibody genes using standard molecular biological techniques that result in variants (agonists) of the antibodies and peptides described herein. Such variants include, but are not limited to deletions, additions and substitutions in the amino acid sequence of the anti-CPAA antibodies or peptides.

For example, one class of substitutions is conserved amino acid substitutions. Such substitutions are those that substitute a given amino acid in an anti-CPAA antibody peptide by another amino acid of like characteristics. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg, replacements among the aromatic residues Phe, Tyr, and the like. Guidance concerning which amino acid changes are likely to be phenotypically silent is found in Bowie et al., 247 Science 1306 (1990).

Variant or agonist anti-CPAA antibodies or peptides may be fully functional or may lack function in one or more activities. Fully functional variants typically contain only conservative variations or variations in non-critical residues or in non-critical regions. Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis. Cunningham et al., 244 Science 1081 (1989). The latter procedure introduces single alanine mutations at every residue in the molecule. The resulting mutant molecules are then tested for biological activity such as epitope binding or in vitro ADCC activity. Sites that are critical for ligand-receptor binding can also be determined by structural analysis such as crystallography, nuclear magnetic resonance, or photoaffinity labeling. Smith et al., 224 J. Mol. Biol. 899 (1992); de Vos et al., 255 Science 306 (1992).

Moreover, polypeptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Proteins—Structure and Molecular Properties (2nd ed., T. E. Creighton, W. H. Freeman & Co., NY, 1993). Many detailed reviews are available on this subject, such as by Wold, POSTTRANSLATIONAL COVALENT MODIF. PROTEINS (Johnson, ed., Acad. Press, N Y, 1983); Seifter et al., 182 Meth. Enzymol. 626 (1990); and Rattan et al., 663 Ann. NY Acad. Sci. 48 (1992).

Accordingly, the antibodies and peptides of the present invention also encompass derivatives or analogs in which a substituted amino acid residue is not one encoded by the genetic code, in which a substituent group is included pegylation as mentioned previously.

Similarly, the additions and substitutions in the amino acid sequence as well as variations, and modifications just described may be equally applicable to the amino acid sequence of the CPAA antigen and/or epitope or peptides thereof, and are thus encompassed by the present invention. As mentioned above, the genes encoding the monoclonal antibody according to the present invention is specifically effective in the recognition of CPAA.

Recombinant Expression of Antibodies

Traditionally, monoclonal antibodies have been produced as native molecules in murine hybridoma lines. In addition to that technology, reviewed below, the present invention provides for recombinant DNA expression of monoclonal antibodies. This allows the production of humanized antibodies as well as spectrum of antibody derivatives and fusion proteins in a host species of choice. More recently, the production of antibodies in bacteria, yeast, transgenic animals and chicken eggs have emerged as promising alternatives for hybridoma-based production systems. The main advantages of transgenic animals are potential high yields from renewable sources.

A nucleic acid sequence encoding at least one anti-CPAA antibody, portion or polypeptide of the present invention may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed, e.g., by Maniatis et al., MOLECULAR CLONING, LAB. MANUAL, (Cold Spring Harbor Lab. Press, N Y, 1982 and 1989), and Ausubel, 1987, 1993, may be used to construct nucleic acid sequences which encode a monoclonal antibody molecule or antigen binding region thereof.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as anti-CPAA peptides or antibody portions in recoverable amounts. The precise nature of the regulatory regions needed for gene expression may vary from organism to organism, as is well known in the analogous art. See, e.g., Sambrook et al., 1989; Ausubel et al., 1987-1993.

The present invention accordingly encompasses the expression of an anti-CPAA antibody or peptide, in either prokaryotic or eukaryotic cells. Suitable hosts include bacterial or eukaryotic hosts including bacteria, yeast, insects, fungi, bird and mammalian cells either in vivo, or in situ, or host cells of mammalian, insect, bird or yeast origin. The mammalian cell or tissue may be of human, primate, hamster, rabbit, rodent, cow, pig, sheep, horse, goat, dog or cat origin, but any other mammalian cell may be used.

Further, by use of, for example, the yeast ubiquitin hydrolase system, in vivo synthesis of ubiquitin-transmembrane polypeptide fusion proteins may be accomplished. The fusion proteins so produced may be processed in vivo or purified and processed in vitro, allowing synthesis of an anti-CPAA antibody or polypeptide of the present invention with a specified amino terminus sequence. Moreover, problems associated with retention of initiation codon-derived methionine residues in direct yeast (or bacterial) expression maybe avoided. Sabin et al., 7 Bio/Technol. 705 (1989); Miller et al., 7 Bio/Technol. 698 (1989).

Any of a series of yeast gene expression systems incorporating promoter and termination elements from the actively expressed genes coding for glycolytic enzymes produced in large quantities when yeast are grown in mediums rich in glucose can be utilized to obtain anti-CPAA antibodies or peptides of the present invention. Known glycolytic genes can also provide very efficient transcriptional control signals. For example, the promoter and terminator signals of the phosphoglycerate kinase gene can be utilized.

Production of anti-CPAA antibodies or peptides or functional derivatives thereof in insects can be achieved, for example, by infecting the insect host with a baculovirus engineered to express a transmembrane polypeptide by methods known to those of skill. See Ausubel et al., 1987, 1993.

In one embodiment, the introduced nucleotide sequence will be incorporated into a plasmid or viral vector capable of autonomous replication in the recipient host. Any of a wide variety of vectors may be employed for this purpose. See, e.g., Ausubel et al., 1987, 1993. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli* (such as, for example, pBR322, ColE1, pSC101, pACYC 184, πVX). Such plasmids are, for example, disclosed by Maniatis et al., 1989; Ausubel et al, 1987, 1993. *Bacillus* plasmids include pC194, pC221, pT127, etc. Such plasmids are disclosed by Gryczan, in THE MOLEC. BIO. OF THE BACILLI 307 (Acad. Press, N Y, 1982). Suitable *Streptomyces* plasmids include pIJ101 (Kendall et al., 169 J. Bacteriol. 4177 (1987)), and *Streptomyces* bacteriophages such as φC31 (Chater et al., in SIXTH INT'L SYMPOSIUM ON ACTINOMYCETALES BIO. 45 (Akademiai Kaido, Budapest, Hungary 1986). *Pseudomonas* plasmids are reviewed in John et al., 8 Rev. Infect. Dis. 693 (1986); Izaki, 33 Jpn. J. Bacteriol. 729 (1978); and Ausubel et al., 1987, 1993.

Alternatively, gene expression elements useful for the expression of cDNA encoding anti-CPAA antibodies or peptides include, but are not limited to (a) viral transcription promoters and their enhancer elements, such as the SV40 early promoter (Okayama et al., 3 Mol. Cell. Biol. 280 (1983)), Rous sarcoma virus LTR (Gorman et al., 79 PNAS 6777 (1982)), and Moloney murine leukemia virus LTR (Grosschedl et al., 41 Cell 885 (1985)); (b) splice regions and polyadenylation sites such as those derived from the SV40 late region (Okayarea et al., 1983), and (c) polyadenylation sites such as in SV40 (Okayama et al., 1983).

Immunoglobulin eDNA genes can be expressed as described by Liu et al., infra, and Weidle et al., 51 Gene 21 (1987), using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA (Whittle et al., 1 Protein Engin. 499 (1987)), the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In one embodiment, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

Each fused gene is assembled in, or inserted into, an expression vector. Recipient cells capable of expressing the chimeric immunoglobulin chain gene product are then transfected singly with an anti-CPAA peptide or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In one embodiment, the fused genes encoding the anti-CPAA peptide or chimeric H and L chains, or portions thereof, are assembled in separate expression vectors that are then used to co-transfect a recipient cell.

Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the fused genes in a bacterial system. The genes so produced and amplified in a bacterial host are subsequently used to co-transfect a eukaryotic cell, and allow selection of a co-transfected cell carrying the desired transfected genes.

Examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo).

Selection of cells expressing gpt is based on the fact that the enzyme encoded by this gene utilizes xanthine as a substrate for purine nucleotide synthesis, whereas the analogous endogenous enzyme can not. In a medium containing (1) mycophenolic acid, which blocks the conversion of inosine monophosphate to xanthine monophosphate, and (2) xanthine, only cells expressing the gpt gene can survive. The product of neo blocks the inhibition of protein synthesis by the antibiotic G418 and other antibiotics of the neomycin class.

These two selection procedures can be used simultaneously or sequentially to select for the expression of immunoglobulin chain genes introduced on two different DNA vectors into a eukaryotic cell. It is not necessary to include different selectable markers for eukaryotic cells; an H and an L chain vector, each containing the same selectable marker can be co-transfected. After selection of the appropriately resistant cells, the majority of the clones will contain integrated copies of both H and L chain vectors and/or anti-CPAA peptides.

Alternatively, the fused genes encoding the chimeric H and L chains can be assembled on the same expression vector.

For transfection of the expression vectors and production of the chimeric antibody, the recipient cell line may be a myeloma cell. Myeloma cells can synthesize, assemble and secrete immunoglobulins encoded by transfected immunoglobulin genes and possess the mechanism for glycosylation of the immunoglobulin. For example the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

The expression vector carrying a chimeric or humanized antibody construct or anti-CPAA polypeptide of the present invention can be introduced into an appropriate host cell by any of a variety of suitable means, including such biochemical means as transformation, transfection, conjugation, protoplast fusion, calcium phosphate-precipitation, and application with polycations such as diethylaminoethyl (DEAF) dextran, and such mechanical means as electroporation, direct microinjection, and microprojectile bombardment. Johnston et al., 240 Science 1538 (1988).

Another way of introducing DNA into lymphoid cells is by electroporation. Potter et al., 81 PNAS 7161 (1984); Yoshikawa et al., 77 Jpn. J. Cancer Res. 1122 (1986). In this procedure, recipient cells are subjected to an electric pulse in the presence of the DNA to be incorporated. Typically, after transfection, cells are allowed to recover in complete medium for about 24 hours, and are then seeded in 96-well culture plates in the presence of the selective medium. G418 selection is performed using about 0.4 mg/ml to 0.8 mg/ml G418. Mycophenolic acid selection utilizes about 6 µg/ml plus about 0.25 mg/ml xanthine. The electroporation technique is expected to yield transfection frequencies of about $10^{-5}$ to about $10^{-4}$ for Sp2/0 cells. In the protoplast fusion method, lysozyme is used to strip cell walls from catarrhal harboring the recombinant plasmid containing the chimeric antibody gene. The resulting spheroplasts are fused with myeloma cells with polyethylene glycol. The immunoglobulin genes of the present invention can also be expressed in nonlymphoid mammalian cells or in other eukaryotic cells, such as yeast, or in prokaryotic cells, in particular bacteria.

Yeast provides substantial advantages over bacteria for the production of immunoglobulin H and L chains. Yeasts carry out post-translational peptide modifications including glycosylation. A number of recombinant DNA strategies now exist which utilize strong promoter sequences and high copy number plasmids which can be used for production of the desired proteins in yeast. Yeast recognizes leader sequences of cloned mammalian gene products and secretes peptides bearing leader sequences (i.e., pre-peptides). Hitzman et al., 11th Intl. Conference on Yeast, Genetics & Molec. Biol. (Montpelier, France, 1982).

Yeast gene expression systems can be routinely evaluated for the levels of production, secretion and the stability of anti-CPAA peptides, antibody and assembled murine and chimeric or humanized antibodies, fragments and regions thereof. Any of a series of yeast gene expression systems incorporating promoter and termination elements from the actively expressed genes coding for glycolytic enzymes produced in large quantities when yeasts are grown in media rich in glucose can be utilized. Known glycolytic genes can also provide very efficient transcription control signals. For example, the promoter and terminator signals of the phosphoglycerate kinase (PGK) gene can be utilized. A number of approaches can be taken for evaluating optimal expression plasmids for the expression of cloned immunoglobulin cDNAs in yeast. See II DNA Cloning 45 (Glover, ed., IRL Press. 1985).

Bacterial strains can also be utilized as hosts for the production of antibody molecules or peptides described by this invention, E. coli K12 strains such as E. coli W3110 (ATCC 27325), and other enterobacteria such as *Salmonella typhimurium* or *Serratia marcescens*, and various *Pseudomonas* species can be used.

Plasmid vectors containing replicon and control sequences which are derived from species compatible with a host cell are used in connection with these bacterial hosts. The vector carries a replication site, as well as specific genes which are capable of providing phenotypic selection in transformed cells. A number of approaches can be taken for evaluating the expression plasmids for the production of murine and chimeric or humanized antibodies, fragments and regions or antibody chains encoded by the cloned immunoglobulin cDNAs in bacteria (see Glover, 1985; Ausubel, 1987, 1993; Sambrook, 1989; Colligan, 1992-1996).

Host mammalian cells may be grown in vitro or in vivo. Mammalian cells provide post-translational modifications to immunoglobulin protein molecules including leader peptide removal, folding and assembly of H and L chains, glycosylation of the antibody molecules, and secretion of functional antibody protein.

Mammalian cells which can be useful as hosts for the production of antibody proteins, in addition to the cells of lymphoid origin described above, include cells of fibroblast origin, such as Vero (ATCC CRL 81) or CHO-K1 (ATCC CRL 61) cells.

Many vector systems are available for the expression of cloned anti-CPAA peptides H and L chain genes in mammalian cells (see Glover, 1985). Different approaches can be followed to obtain complete $H_2 L_2$ antibodies. As discussed above, it is possible to co-express H and L chains in the same cells to achieve intracellular association and linkage of H and L chains into complete tetrameric $H_2 L_2$ antibodies and/or anti-CPAA peptides. The co-expression can occur by using either the same or different plasmids in the same host. Genes for both H and L chains and/or anti-CPAA peptides can be placed into the same plasmid, which is then transfected into cells, thereby selecting directly for cells that express both chains. Alternatively, cells can be transfected first with a plasmid encoding one chain, for example the L chain, followed by transfection of the resulting cell line with an H chain plasmid containing a second selectable marker. Cell lines producing anti-CPAA peptides and/or $H_2 L_2$ molecules via either route could be transfected with plasmids encoding additional copies of peptides, H, L, or H plus L chains in conjunction with additional selectable markers to generate cell lines with enhanced properties, such as higher production of assembled $H_2 L_2$ antibody molecules or enhanced stability of the transfected cell lines.

Additionally, plants have emerged recently as a convenient, safe and economical alternative main-stream expression systems for recombinant antibody production, which are based on large scale culture of microbes or animal cells. Antibodies may be expressed in plant cell culture, or plants grown conventionally. The expression in plants may be systemic, limited to susb-cellular plastids, or limited to seeds (endosperms). See, e.g., U.S. Patent Appl. Pub. No. 2003/0167531; U.S. Pat. No. 6,080,560 and No. 6,512,162; WO 0129242. Several plant-derived antibodies have reached advanced stages of development, including clinical trials (see, e.g., Biolex, NC).

Hybridoma Technology

The present invention provides for a hybridoma cell line that produces a monoclonal antibody that has a high degree of specificity and affinity towards CPAA. The present invention relates also to variants and mutants of the hybridoma cell lines characterized in detail above that which occur spontaneously or that can be produced artificially using known methods and that still have the characteristic properties of the starting material, that is to say are still capable of producing the antibodies according to the invention or derivatives thereof and secreting them into the surrounding medium.

The present invention also includes methods for the production of said hybridoma cell lines and to methods for the production of said monoclonal antibodies. Clones and sub-clones of hybridoma cell lines are to be understood as being hybridomas that are produced from the starting clone by repeated cloning and that still have the features of the starting clone that are essential to the invention.

More specifically, nucleic acid, protein or peptide molecules of the invention may be utilized to develop monoclonal or polyclonal antibodies that bind CPAA. For preparation of the CPAA-binding antibodies of the present invention, any technique which provides for the production of antibody molecules by continuous cell lines in culture may be used. For example, the hybridoma technique originally developed by Kohler and Milstein (256 Nature 495 (1975)) may be used. See also U.S. Pat. No. 4,376,110; Ausubel et al., 1988; CURR. PROT. IMMUNOL. (Colligan et al., eds., Greene Pub. Assoc. & Wiley Intersci. NY, 1992-1996).

Another advantageous route for creating high affinity and/or high avidity human antibodies involves antigen priming of native human splenocytes in vitro, transferral of the resultant in vitro antigen primed splenocyte cells to an immunocompromised donor, e.g., a SCID mouse, boosting the immunocompromised donor with antigen, isolating human antibody secreting B-cells (IgG secreting) from the donor, and EBV-transforming the isolated human antibody secreting cells, as described in U.S. Pat. No. 6,537,809.

Chimeric Humanized and Fully Humanized Antibodies

The antibodies of the present invention include chimeric antibodies comprising part human and part mouse antibodies, in which the constant region from human antibodies are cloned to a variable regions of light and heavy chains from mouse. In some instances, 70% of the human sequences are retained. Humanized antibodies are chimeric antibodies in which perhaps 90% of the human antibody framework is retained, and combined only with the murine the complementary determining regions. Fully humanized antibodies are also contemplated in the present invention.

Recombinant murine or chimeric murine-human or human-human antibodies that bind an epitope included in the amino acid sequences of CPAA can be provided according to the present invention using known techniques based on the teaching provided herein. See, e.g., Ausubel et al., 1987, 1992, and 1993; Sambrook et al., 1989. For example, an antibody may be humanized by grafting the desired CDRs onto a human framework according to EP0239400.

The DNA encoding an anti-CPAA antibody of the present invention can be genomic DNA or cDNA which encodes at least one of the heavy chain constant region ($H_c$), the heavy chain variable region ($H_v$), the light chain variable region ($L_v$) and the light chain constant regions ($L_c$). A convenient alternative to the use of chromosomal gene fragments as the source of DNA encoding the murine V region antigen-binding segment is the use of cDNA for the construction of chimeric immunoglobulin genes. See e.g., Liu et al. 84 PNAS 3439 (1987); 139 J. Immunol. 3521 (1987). The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding murine V and C region antigen-binding segments having anti-CPAA activity can be provided using known methods based on the use of the DNA sequences presented in FIG. 2-FIG. 5. Probes that bind a portion of the DNA sequences presented in FIG. 2 or FIG. 3 can be used to isolate DNA from hybridomas expressing anti-CPAA antibodies, fragments or regions, as presented herein, according to the present invention, by known methods.

Oligonucleotides representing the CPAA-binding antibodies light and heavy chains, presented in FIG. 2 and FIG. 3 useful for screening for the presence of homologous genes and for the cloning of such genes encoding variable or constant regions of an anti-CPAA antibody. Such probes usually bind to DNA sequences (cDNA, genomic DNA, or any other DNA) that encode the amino acid sequences underlined in FIG. 4 and FIG. 5 to the light chain or heavy chain CDR regions which bind an epitope of CPAA. Such techniques for synthesizing such oligonucleotides are well known. See, e.g., Wu et al., 21 Prog. Nucl. Acids Res. Molec. Biol. 101 (1978); Ausubel et al., 1987, 1993.

In an alternative way of cloning a polynucleotide encoding an anti-CPAA variable or constant region, a library of expression vectors is prepared by cloning DNA or cDNA (from a cell capable of expressing an anti-CPAA antibody or variable or constant region) into an expression vector. The library is then screened for members capable of expressing a protein which competitively inhibits the binding of an anti-CPAA antibody, such as A2 or cA2, and which has a nucleotide sequence that is capable of encoding peptides that have the same amino acid sequence as anti-CPAA. antibodies or fragments thereof. In this embodiment, DNA, such as cDNA, is extracted and purified from a cell which is capable of expressing an anti-CPAA antibody or fragment. The purified cDNA is fragmentized (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment such as in a lambda phage library, expression in prokaryotic cell (e.g., bacteria) or eukaryotic cells, (e.g., mammalian, yeast, insect or, fungus). See, e.g., Ausubel, 1987, 1993; Harlow, 1988; Colligan, 1992-1996; Nyyssonen et al. 11 Bio/Technology 591 (1993); Marks et al., 11 Bio/Technology 1145 (1993).

Once nucleic acid encoding such variable or constant anti-CPAA regions is isolated, the nucleic acid can be appropriately expressed in a host cell, along with other constant or variable heavy or light chain encoding nucleic acid, in order to provide recombinant monoclonal antibodies that bind CPAA with inhibitory activity. Such antibodies may include a murine or human anti-CPAA variable region which contains a framework residue having complementarity determining residues which are responsible for antigen binding. In one embodiment, an anti-CPAA variable light or heavy chain encoded by a nucleic acid as described above binds an epitope of at least five amino acids. The amino acid sequences of such anti-CPAA variable light or heavy chains are underlined in FIG. 4, FIG. 5, and FIG. 12.

Human genes which encode the constant (C) regions of the murine and chimeric antibodies, fragments and regions of the present invention can be derived from a human fetal liver library, by known methods. Human C regions genes can be derived from any human cell including those which express and produce human immunoglobulins. The human $C_H$ region can be derived from any of the known classes or isotypes of human H chains, including γ, μ, α, δ or ε, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). For example, the $C_H$ region is derived from γ1 (IgG1), γ3 (IgG3), γ4 (IgG4), or μ (IgM). The human $C_L$ region can be derived from either human L chain isotype, kappa or lambda.

Genes encoding human immunoglobulin C regions are obtained from human cells by standard cloning techniques (Sambrook et al., 1989; Ausubel et al., 1987, 1993). Human C region genes are readily available from known clones containing genes representing the two classes of L chains, the five classes of H chains and subclasses thereof. Chimeric antibody fragments, such as F(ab')$_2$ and Fab, can be prepared by designing a chimeric H chain gene which is appropriately truncated. For example, a chimeric gene encoding an H chain portion of an F(ab')$_2$ fragment would include DNA sequences encoding the $CH_1$ domain and hinge region of the H chain, followed by a translational stop codon to yield the truncated molecule.

Generally, the murine, human or murine and chimeric antibodies, fragments and regions of the present invention are produced by cloning DNA segments encoding the H and L chain antigen-binding regions of a CPAA-specific antibody, and joining these DNA segments to DNA segments encoding $C_H$ and $C_L$ regions, respectively, to produce murine, human or chimeric immunoglobulin-encoding genes.

Thus, in one embodiment, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions, the method of producing the chimeric antibody according to the present invention involves several steps, outlined below:

isolation of messenger RNA (mRNA) from the cell line producing an anti-CPAA antibody and from optional additional antibodies supplying heavy and light constant regions; cloning and cDNA production therefrom;

preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody;

Construction of complete H or L chain coding sequences by linkage of the cloned specific V region gene segments to cloned C region gene, as described above;

Expression and production of L and H chains in selected hosts, including prokaryotic and eukaryotic cells to provide murine-murine, human-murine, human-human or human murine antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C ($C_k$) region and the complete human gamma-1 C region ($C_{\gamma-1}$). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human $C_{\gamma-1}$ region can be modified by introducing a termination codon thereby generating a gene sequence which encodes the H chain portion of a Fab molecule. The coding sequences with linked V and C regions are then transferred into appropriate expression vehicles for expression in appropriate hosts: prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Among these are vehicles carrying a functionally complete human $C_H$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C region; polyadenylation and transcription termination occur at native chromosomal sites downstream of the human coding regions. See U.S. Pat. No. 6,835,823.

"Fully humanized antibodies" against CPAA are also contemplated in the present invention. Fully humanized antibodies are molecules containing both the variable and constant region of the human immunoglobulin. Fully humanized antibodies can be potentially used for therapeutic use, where repeated treatments are required for chronic and relapsing diseases such as autoimmune diseases. One method for the preparation of fully human antibodies consist of "humanization" of the mouse humoral immune system, i.e. production of mouse strains able to produce human Ig (Xenomice), by the introduction of human immunoglobulin (Ig) loci into mice in which the endogenous Ig genes have been inactivated. The Ig loci are exceedingly complex in terms of both their physical structure and the gene rearrangement and expression processes required to ultimately produce a broad immune response. Antibody diversity is primarily generated by combinatorial rearrangement between different V, D, and J genes present in the Ig loci. These loci also contain the interspersed regulatory elements, which control antibody expression, allelic exclusion, class switching and affinity maturation. Introduction of unrearranged human Ig transgenes into mice has demonstrated that the mouse recombination machinery is compatible with human genes. Furthermore, hybridomas secreting antigen specific hu-mAbs of various isotypes can be obtained by Xenomice immunization with antigen. Fully humanized antibodies and methods for their production are known in the art. See, e.g., U.S. Pat. No. 7,276,239 and No. 6,835,823.

An aspect of the present invention provides for the production of a humanized antibody, which is prepared according to the invention by a process which comprises maintaining a host transformed with a first expression vector which encodes the light chain of the humanized antibody and with a second expression vector which encodes the heavy chain of the humanized antibody under such conditions that each chain is expressed and isolating the humanized antibody formed by assembly of the thus-expressed chains. The first and second expression vectors may be the same vector. The invention further provides: a DNA sequence encoding the light chain or the heavy chain of the humanized antibody; an expression vector which incorporates a said DNA sequence; and a host transformed with a said expression vector.

Generating a humanized antibody from the sequences provided herein can be practiced by those of ordinary skill in the art without undue experimentation. In one approach, there are four general steps employed to humanize a monoclonal antibody, see, e.g., U.S. Pat. No. 5,585,089; No. 6,835,823; and No. 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

Regarding the nucleotide and predicted amino acid sequences, there are two general methods for cloning a given antibody's heavy and light chain variable domain cDNAs: (a) via a conventional cDNA library, or (b) via the polymerase chain reaction (PCR). Both of these methods are widely known, see, e.g., U.S. Patent Appl. Pub. No. 2003/0166871. Given the nucleotide sequence of the cDNAs, it is a simple matter to translate this information into the predicted amino acid sequence of the antibody variable domains. In the present instance, the nucleotide sequence of the light and heavy chains of the 16C3 antibody are shown in FIG. 2 and FIG. 3, respectively. The predicted amino acid sequence of the light and heavy chains of the 16C3 antibody are shown in FIG. 4 and FIG. 5, respectively.

Regarding the design of the humanized antibody, there are several factors to consider in deciding which human antibody sequence to use during the humanization. The humanization of light and heavy chains are considered independently of one another, but the reasoning is basically similar for each. This selection process is based on the following rationale: A given antibody's antigen specificity and affinity is primarily determined by the amino acid sequence of the variable region CDRs. Variable domain framework residues have little or no direct contribution. The primary function of the framework regions is to hold the CDRs in their proper spatial orientation to recognize antigen. Thus, the substitution of rodent CDRs such as those underlined in FIG. 4 or FIG. 5 into a human variable domain framework is most likely to result in retention of their correct spatial orientation if the human variable domain framework is highly homologous to the rodent variable domain from which they originated. A human variable domain may be chosen, therefore, that is highly homologous to the rodent variable domain(s).

A suitable human antibody variable domain sequence can be selected as follows:

1. Using a computer program, search all available protein (and DNA) databases for those human antibody variable domain sequences that are most homologous to the rodent antibody variable domains. The output of a suitable program is a list of sequences most homologous to the rodent antibody, the percent homology to each sequence, and an alignment of each sequence to the rodent sequence. This is done independently for both the heavy and light chain variable domain sequences. The above analyses are more easily accomplished if only human immunoglobulin sequences are included.
2. List the human antibody variable domain sequences and compare for homology. Primarily, the comparison is performed on length of CDRs, except CDR3 of the heavy chain which is quite variable. Human heavy chains and Kappa and Lambda light chains are divided into subgroups; Heavy chain 3 subgroups, Kappa chain 4 subgroups, Lambda chain 6 subgroups. The CDR sizes within each subgroup are similar but vary between subgroups. It is usually possible to match a rodent antibody CDR to one of the human subgroups as a first approximation of homology. Antibodies bearing CDRs of similar length are then compared for amino acid sequence homology, especially within the CDRs, but also in the surrounding framework regions. The human variable domain which is most homologous is chosen as the framework for humanization.

The actual humanizing methodologies and techniques are also within the grasp of those of ordinary skill in the art. A DNA sequence encoding the desired reshaped antibody can therefore be made beginning with the human DNA whose CDRs it is wished to reshape. The rodent variable domain amino acid sequence containing the desired CDRs is compared to that of the chosen human antibody variable domain sequence. The residues in the human variable domain are marked that need to be changed to the corresponding residue in the rodent to make the human variable region incorporate the rodent CDRs. There may also be residues that need substituting in, adding to or deleting from the human sequence.

Oligonucleotides are synthesized that can be used to mutagenize the human variable domain framework to contain the desired residues. Those oligonucleotides can be of any convenient size. One is normally only limited in length by the capabilities of the particular synthesizer one has available. The method of oligonucleotide-directed in vitro mutagenesis is well known.

Alternatively, humanization may be achieved using the recombinant polymerase chain reaction (PCR) methodology of U.S. Pat. No. 5,858,725. Using this methodology, a CDR may be spliced between the framework regions of a human antibody. In general, the technique of U.S. Pat. No. 5,858,725 can be performed using a template comprising two human framework regions, AB and CD, and between them, the CDR which is to be replaced by a donor CDR. Primers A and B are used to amplify the framework region CD. However, the primers B and C each also contain, at their 5' ends, an additional sequence corresponding to all or at least part of the donor CDR sequence. Primers B and C overlap by a length sufficient to permit annealing of their 5' ends to each other under conditions which allow a PCR to be performed. Thus, the amplified regions AB and CD may undergo gene splicing by overlap extension to produce the humanized product in a single reaction.

Alternatively, humanization may be achieved by chemical synthesis of the DNAs encoding the humanized immunoglobulin proteins, or fragments thereof, and using standard molecular biology techniques to amplify and subclone the synthetic genes into an appropriate expression vector. In this case, multiple sense and antisense oligonucleotides with overlapping sequences that encompass the entire coding region of the humanized antibody genes are chemically synthesized and purified. The oligonucleotides are then mixed together such that the overlapping sense strand oligonucleotides can anneal to their antisense strand partners, and the entire gene can be amplified to sufficient quantity using the polymerase chain reaction. The target genes can then be cloned into an expression plasmid using conveniently engineered restriction enzymes.

Several light and heavy chain sequences for the humanized 16C3 antibody, designed according to various techniques as described herein, are presented in FIG. 6, FIG. 7, and FIG. 12. More specifically, five different designs for converting the murine 16C3 antibody to a humanized, therapeutically useful antibody are presented. The designs are based upon structural information about known murine and human antibody sequences. For example, referring to FIG. 6 and FIG. 7, "ven16C3" has been veneered with human framework sequences, "cdr16C3" has been remodeled with human CDR amino acids, "abb16C3" represents abbreviated CDR grafting, "sdr16C3" represents site determining amino acid changes, and "fra16C3" represents a "Frankenstein" approach to remodeling the variable region by using a combination of various "pieces" of human variable regions. Human germline IgG sequences were used for the framework sequences.

Additionally, as described in the Examples below, a recombinant humanized antibody may be further optimized to decrease potential immunogenicity, while maintaining functional activity, for therapy in humans. In this regard, functional activity means a polypeptide capable of displaying one or more known functional activities associated with a 16C3 antibody of the invention. Such functional activities include, biological activity, and ability to bind to a ligand for a 16C3 polypeptide. Additionally, a polypeptide having functional activity means the polypeptide exhibits activity similar, but not necessarily identical to, an activity of a 16C3 polypeptide of the present invention, including mature forms, as measured in a particular assay, such as, for example, a biological assay, with or without dose dependency. In the case where dose dependency does exist, it need not be identical to that of the 16C3 polypeptides, but rather substantially similar to the dose-dependence in a given activity as compared to the 16C3 polypeptides of the present invention (i.e., the candidate polypeptide will exhibit greater activity, or not more than about 25-fold less, about 10-fold less, or about 3-fold less activity relative to the 16C3 polypeptides of the present invention).

The optimized humanized 16C3 antibody, designated H16C3-Abb*, comprises the amino acid residues shown in FIG. 12. Note that some of the amino acid residues within the antibody CDRs have been changed from those present in the original murine CDRs. The different CDRs are considered examples of variants of each other, having functional equivalence, within the scope of the present application.

Following the mutagenesis reactions to reshape the antibody, the mutagenized DNAs can be linked to an appropriate DNA encoding a light or heavy chain constant region, cloned into an expression vector, and transfected into host cells, such as mammalian cells. These steps can be carried out in routine fashion. A reshaped antibody may therefore be prepared by a process comprising:

(a) preparing a first replicable expression vector including a suitable promoter operably linked to a DNA sequence which encodes at least a variable domain of an Ig heavy or light chain, the variable domain comprising framework regions from a human antibody and the CDRs required for the humanized antibody of the invention;

(b) preparing a second replicable expression vector including a suitable promoter operably linked to a DNA sequence which encodes at least the variable domain of a complementary Ig light or heavy chain, respectively;

(c) transforming a cell line with the first or both prepared vectors; and (d) culturing said transformed cell line to produce said altered antibody.

The DNA sequence in step (a) may encode both the variable domain and/or each constant domain of the human antibody chain. The humanized antibody can be prepared using any suitable recombinant expression system. The cell line that is transformed to produce the altered antibody may be a Chinese Hamster Ovary (CHO) cell line or an immortalized mammalian cell line, which is advantageously of lymphoid origin, such as a myeloma, hybridoma, trioma or quadroma cell line. The cell line may also comprise a normal lymphoid cell, such as a B-cell, which has been immortalized by transformation with a virus, such as the Epstein-Barr virus. For example, the immortalized cell line is a myeloma cell line or a derivative thereof.

The CHO cells used for expression of the antibodies according to the invention may be dihydrofolate reductase (dhfr) deficient and so dependent on thymidine and hypoxanthine for growth. See Urlaub et al., 77 PNAS 4216 (1980). The parental dhfr CHO cell line is transfected with the DNA encoding the antibody and dhfr which enables selection of CHO cell transfectants of dhfr positive phenotype. Selection is carried out by culturing the colonies on media devoid of thymidine and hypoxanthine, the absence of which prevents untransfected cells from growing and transformed cells from resalvaging the folate pathway and thus bypassing the selection system. These transfectants usually express low levels of the DNA of interest by virtue of co-integration of transfected DNA of interest and DNA encoding dhfr. The expression levels of the DNA encoding the antibody may be increased by amplification using methotrexate (MTX). This drug is a direct inhibitor of the enzyme dhfr and allows isolation of resistant colonies which amplify their dhfr gene copy number sufficiently to survive under these conditions. Since the DNA sequences encoding dhfr and the antibody are closely linked in the original transfectants, there is usually concomitant amplification, and therefore increased expression of the desired antibody.

Another expression system for use with CHO or myeloma cells is the glutamine synthetase (GS) amplification system described in, for example, U.S. Pat. No. 5,122,464. This system involves the transfection of a cell with DNA encoding the enzyme GS and with DNA encoding the desired antibody. Cells are then selected which grow in glutamine free medium and can thus be assumed to have integrated the DNA encoding GS. These selected clones are then subjected to inhibition of the enzyme GS using methionine sulphoximine ($M_{SX}$). The cells, in order to survive, will amplify the DNA encoding GS with concomitant amplification of the DNA encoding the antibody.

Although the cell line used to produce the humanized antibody may be a mammalian cell line, any other suitable cell line, such as a bacterial cell line or a yeast cell line, may alternatively be used. For example, in instances requiring no in vivo post-translational modification (such as instances where glycosylation is not required), it is envisaged that *E. coli*-derived bacterial strains could be used. The antibody obtained is checked for functionality. If functionality is lost, it is necessary to return to step (2) and alter the framework of the antibody.

Once expressed, the whole antibodies, their dimers, individual light and heavy chains, or other immunoglobulin forms of the present invention can be recovered and purified by known techniques, e.g., immunoabsorption or immunoaffinity chromatography, chromatographic methods such as HPLC (high performance liquid chromatography), ammonium sulfate precipitation, gel electrophoresis, or any combination of these. See generally, Scopes, PROT. PURIF. (Springer-Verlag, NY, 1982). Substantially pure immunoglobulins of at least about 90% to 95% homogeneity are advantageous, as are those with 98% to 99% or more homogeneity, particularly for pharmaceutical uses. Once purified, partially or to homogeneity as desired, a humanized antibody may then be used therapeutically or in developing and performing assay procedures, immunofluorescent stainings, and the like. See generally, Vols. I & II Immunol. Meth. (Lefkovits & Pernis, eds., Acad. Press, N Y, 1979 and 1981).

Phage Libraries and Alternative Recombinant Expression Systems

Along with the above production techniques, in vitro systems such as phage display methods of fully human antibodies and antibody peptides, many of the benefits of human antibodies as both diagnostics and therapeutics are now being realized.

The recombinant antibody and its sequences of the present invention allows for the construction of a myriad of derivatives and ligand binding molecules with anti-PCAA binding activity. For example, the CDRs may be recombined with an antibody library such as the n-CoDeR human scFV library to create highly specific and functional antibody fragments. See Moore, 426 Nature, 725 (2003).

A library of fully human antibodies or portions thereof may also be created following the cloning methods based on site specific cleavage of single-stranded DNAs as described by U.S. Patent Appl. Pub. No. 2003/0232333.

Another ligand binding molecule that may be constructed from the DNA sequence information contained herein, and the associated knowledge gained about the PCAA epitopes provided by the invention herein, involves the construction of ANTICALINS® lipocalins, a widespread group of small and robust proteins that are usually involved in the physiological transport or storage of chemically sensitive or insoluble compounds. Several natural lipocalins occur in human tissues or body liquids. Despite low mutual sequence homology, the lipocalins share a structurally conserved β-barrel supporting four loops at one end, which form the entrance to a binding pocket. The loops exhibit large conformational differences between individual lipocalins and give rise to the variety of natural ligand specificities. This protein architecture is reminiscent of immunoglobulins, with their hypervariable loops on top of a rigid framework. Unlike antibodies or some antibody fragments, lipocalins are composed of a single polypeptide chain with 160 to 180 amino acid residues, being just marginally bigger than a single immunoglobulin domain. The set of four loops that makes up the binding pocket shows structural plasticity and tolerates a variety of side chains. The binding site can thus be reshaped in order to recognize prescribed target molecules of different shape with high affinity and specificity. ANTICALINS® lipocalins have been engineered that recognize hapten-like compounds, peptides, and protein targets, e.g. extracellular domains of cell surface receptors. Fusion proteins with enzymes and also bispecific binding proteins (so-called DUOCALINS® bispecific binding proteins, Pieris AG, Freising-Weihenstephan, Germany) have also been successfully prepared. Pre-clinical experiments have been conducted. See, e.g., Korndörfer et al., 330 J. Mol. Biol. 385-96 (2003).

Another antibody type with application to the invention described herein include the camilid immunoglobulins which possess functional heavy chains and lack light chains. These antibodies are assembled from dedicated V and C gamma genes. They have been cloned and adapted using phage display technology to produce antigen-specific single-domain antibody fragments with intrinsic high stability. U.S. Patent Appl. Pub. No. 2003/0088074.

Another relevant derivative takes advantage of new technology for providing bacterially produced antibody fragments that can crosslink antigen and antibody effector molecules (Fc-region molecules), called PEPBODIES™ antibody fragments. See U.S. Patent Appl. Pub. No. 2004/0101905. Hence, the binding molecules comprising the antigen binding site of the anti-PCAA site is genetically fused to peptides that display one or more of the effector functions associated with the Fc-region, and provides for functions such as interaction with cell receptors and complement activation.

The new antigen receptor (IgNAR) molecules from sharks may also be considered a "derivative" antibody molecule. The NAR is a disulphide bonded dimer of two protein chains, each containing one variable and five constant domains, and functions as an antibody. Nuttall et al., 270 Eur. J. Biochem., 3543 (2003). The sequences of the PCAA-binding antibody of the present invention may be constructed into the NAR variable region to create an in vitro library incorporating synthetic the CDR regions. This results in a single domain binding reagent.

One of the recent advances in cancer cell biology entails the discovery of progenitor cell lines that may exhibit cancer-cell markers. For example, human pancreatic epithelial progenitor cells have been identified and grown in culture. These cells may then be used for the generation of antigens useful, inter cilia, for the development of monoclonal antibodies. U.S. Pat. No. 6,436,704. Thus, the PCAA-binding antibody may be used to identify progenitor cells. These progenitor cells can be used as an immunogen that is administered to a heterologous recipient, such as a mouse, for derivation of further lines of PCAA-binding antibodies.

In conclusion, the oligonucleotide and amino acid sequences provided herein enable a myriad of possible molecules with CPAA-binding activity, and the scope of the present invention is not limited by the methods of achieving those molecules.

Antibody Derivatives

A "derivative" of an antibody contains additional chemical moieties not normally a part of the protein. Covalent modifications of the protein are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers.

Derivatives also include radioactively labeled monoclonal antibodies that are labeled, for example, with radioactive iodine ($^{125}$I, $^{131}$I) carbon ($^{14}$C), sulfur ($^{35}$S), indium ($^{111}$In), tritium ($^{3}$H) or the like; conjugates of monoclonal antibodies with biotin or avidin, with enzymes, such as horseradish peroxidase, alkaline phosphatase, β-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters) or fluorescent agents (such as phycobiliproteins). An example of a derivative of the antibody of the invention is an antibody-small molecule drug conjugate, such as an antibody-maytansinoid conjugate, that displays cytotoxic activity. See U.S. Patent Appl. Pub. No. 2004/0039176. Preclinical evaluation has shown that this conjugate acts as a tumor-activated prodrug that exhibits potent antitumor activity in xenograft models. Further cytotoxic antibody derivatives are discussed below.

Another derivative bifunctional antibody of the present invention is a bispecific antibody, generated by combining parts of two separate antibodies that recognize two different antigenic groups. This may be achieved by crosslinking or recombinant techniques. Additionally, moieties may be added to the antibody or a portion thereof to increase half-life in vivo (e.g., by lengthening the time to clearance from the blood stream. Such techniques include, for example, adding PEG moieties (also termed pegilation), and are well-known in the art. See U.S. Patent. Appl. Pub. No. 2003/0031671.

Anti-Idiotype Abs

In addition to monoclonal or chimeric anti-CPAA antibodies, the present invention is also directed to an anti-idiotypic (anti-Id) antibody specific for the anti-CPAA antibody of the invention. An anti-Id antibody is an antibody which recognizes unique determinants generally associated with the antigen-binding region of another antibody. The antibody specific for CPAA is termed the idiotypic or Id antibody. The anti-Id can be prepared by immunizing an animal of the same species and genetic type (e.g., mouse strain) as the source of the Id antibody with the Id antibody or the antigen-binding region thereof. The immunized animal will recognize and respond to the idiotypic determinants of the immunizing antibody and produce an anti-Id antibody. The anti-Id antibody can also be used as an "immunogen" to induce an immune response in yet another animal, producing a so-called anti-anti-Id antibody. The anti-anti-Id can be epitopically identical to the original antibody which induced the anti-Id. Thus, by using antibodies to the idiotypic determinants of a mAb, it is possible to identify other clones expressing antibodies of identical specificity.

Accordingly, monoclonal antibodies generated against CPAA according to the present invention can be used to induce anti-Id antibodies in suitable animals, such as BALB/c mice. Spleen cells from such immunized mice can be used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the original mAb specific for a CPAA epitope.

Idiotypes, Anti-Idiotypes

Additionally, antibodies against CPAA, its analogs, portions, fragments, peptides or derivatives thereof may be used to induce anti-Id antibodies in suitable animals, such as BALM mice. Spleen cells from such immunized mice are used to produce anti-Id hybridomas secreting anti-Id monoclonal antibodies. Further, the anti-Id antibodies can be coupled to a carrier such as keyhole limpet hemocyanin (KLH) and used to immunize additional BALB/c mice. Sera from these mice will contain anti-anti-Id antibodies that have the binding properties of the original monoclonal antibody specific for an epitope of CPAA, or analogs, fragments and derivatives thereof. The anti-Id antibodies thus have their own idiotypic epitopes, or "idiotopes" structurally similar to the epitope being evaluated.

An anti-idiotypic (anti-Id) antibody is an antibody that recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, e.g., U.S. Pat. No. 4,699,880 and No. 6,835,823. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Structural Analogs of Anti-CPAA Antibodies and Anti-CPAA Peptides

Structural analogs of anti-CPAA antibodies and peptides of the present invention are provided by known method steps based on the teaching and guidance presented herein.

Knowledge of the three-dimensional structures of proteins is crucial in understanding how they function. The three-dimensional structures of hundreds of proteins are currently available in protein structure databases (in contrast to the thousands of known protein sequences in sequence databases). Analysis of these structures shows that they fall into recognizable classes of motifs. It is thus possible to model a three-dimensional structure of a protein based on the protein's homology to a related protein of known structure. Many examples are known where two proteins that have relatively low sequence homology, can have very similar three dimensional structures or motifs.

In recent years it has become possible to determine the three dimensional structures of proteins of up to about 15 kDa by nuclear magnetic resonance (NMR). The technique requires a concentrated solution of pure protein: no crystals or isomorphous derivatives are needed. The structures of a number of proteins have been determined by this method. The details of NMR structure determination are well-known in the art. See, e.g., Wuthrich, NMR OF PROTEINS & NUCLEIC ACIDS (Wiley, N.Y., 1986); Wuthrich, 243 Science 45 (1989); Clore et al., 24 Critical Rev. Biochem. Molec. Biol. 479 (1989); Cooke et al., 8 Bioassays 52 (1988).

In applying this approach, a variety of $^1$H NMR 2D data sets are collected for anti-CPAA antibodies and/or anti-CPAA peptides of the present invention. These are of two main types. One type, COSY (Correlated Spectroscopy) identifies proton resonances that are linked by chemical bonds. These spectra provide information on protons that are linked by three or less covalent bonds. NOESY (nuclear Overhauser enhancement spectroscopy) identifies protons which are close in space (less than 0.5 nm). Following assignment of the complete spin system, the secondary structure is defined by NOESY. Cross peaks (nuclear Overhauser effects or NOE's) are found between residues that are adjacent in the primary sequence of the peptide and can be seen for protons less than 0.5 nm apart. The data gathered from sequential NOE's combined with amide proton coupling constants and NOE's from non-adjacent amino acids that are adjacent to the secondary structure, are used to characterize the secondary structure of the peptides. Aside from predicting secondary structure, NOE's indicate the distance that protons are in space in both the primary amino acid sequence and the secondary structures. Tertiary structure predictions are determined, after all the data are considered, by a "best fit" extrapolation.

Types of amino acids are first identified using through-bond connectivities. Next, specific amino acids are assigned using through-space connectivities to neighboring residues, together with the known amino acid sequence. Structural information is then tabulated and is of three main kinds: The NOE identifies pairs of protons which are close in space, coupling constants give information on dihedral angles and slowly exchanging amide protons give information on the position of hydrogen bonds. The restraints are used to compute the structure using a distance geometry type of calculation followed by refinement using restrained molecular dynamics. The output of these computer programs is a family of structures which are compatible with the experimental data (i.e. the set of pairwise <0.5 nm distance restraints). The better that the structure is defined by the data, the better the family of structures can be superimposed, (i.e., the better the resolution of the structure). In the better defined structures using NMR, the position of much of the backbone (i.e., the amide, C$\alpha$ and carbonyl atoms) and the side chains of those amino acids that lie buried in the core of the molecule can be defined as clearly as in structures obtained by crystallography. The side chains of amino acid residues exposed on the surface are frequently less well defined, however. This probably reflects the fact that these surface residues are more mobile and can have no fixed position. (In a crystal structure this might be seen as diffuse electron density).

Thus, according to the present invention, use of NMR spectroscopic data is combined with computer modeling to arrive at structural analogs of at least portions of anti-CPAA antibodies and peptides based on a structural understanding of the topography. Using this information, one of ordinary skill in the art will know how to achieve structural analogs of anti-CPAA antibodies or peptides, such as by rationally-based amino acid substitutions allowing the production of peptides in which the CPAA binding affinity or avidity is modulated in accordance with the requirements of the expected therapeutic or diagnostic use of the molecule, for example, the achievement of greater specificity for CPAA binding.

Alternatively, compounds having the structural and chemical features suitable as anti-CPAA therapeutics and diagnostics provide structural analogs with selective CPAA affinity. Molecular modeling studies of CPAA binding compounds, such as CPAA receptors, anti-CPAA antibodies, or other CPAA binding molecules, using a program such as MacroModel® (Schrödinger, LLC, NY), Insight® II and Discover® (Accelrys Software Inc., Burlington, Mass.), provide such spatial requirements and orientation of the anti-CPAA Abs and/or peptides according to the present invention. Such structural analogs of the present invention thus provide selective qualitative and quantitative anti-CPAA activity in vitro, in situ and/or in vivo.

Diagnostic Applications

The present invention also provides the above anti-CPAA antibodies and peptides for use in diagnostic methods for detecting CPAA in patients known to be or suspected of having pancreatic or colon carcinoma. In another aspect of the invention, the antibodies may detect molecular markers in morphologically normal cells to provide for early detection screening of disease-free individuals.

Anti-CPAA antibodies and/or peptides of the present invention are useful for immunoassays which detect or quantitate CPAA, or anti-CPAA antibodies, in a sample. An immunoassay for CPAA typically comprises incubating a clinical or biological sample in the presence of a detectably labeled high affinity (or high avidity) anti-CPAA antibody or polypeptide of the present invention capable of selectively binding to CPAA, and detecting the labeled peptide or antibody which is bound in a sample. Various clinical assay procedures are well known in the art. See, e.g., IMMUNOASSAYS FOR THE 80's (Voller et al., eds., Univ. Park. 1981). Such samples include tissue biopsy, blood, serum, and fecal samples, or liquids collected from the colorectal track following enema, colonoscopy, or oral laxative solution and subjected to ELISA analysis as described below.

Thus, an anti-CPAA antibody or polypeptide can be fixed to nitrocellulose, or another solid support which is capable of immobilizing cells, cell particles or soluble proteins. The support can then be washed with suitable buffers followed by treatment with the detectably labeled CPAA-specific peptide or antibody. The solid phase support can then be washed with the buffer a second time to remove unbound peptide or antibody. The amount of bound label on the solid support can then be detected by known method steps.

"Solid phase support" or "carrier" refers to any support capable of binding peptide, antigen, or antibody. Well-known supports or carriers, include glass, polystyrene, polypropylene, polyethylene, polyvinylidenefluoride (PVDF), dextran, nylon, amylases, natural and modified celluloses, polyacrylamides, agaroses, and magnetite. The nature of the carrier can be either soluble to some extent or insoluble for the purposes of the present invention. The support material can have virtually any possible structural configuration so long as the coupled molecule is capable of binding to CPAA or an anti-CPAA antibody. Thus, the support configuration can be spherical, as in a bead, or cylindrical, as in the inside surface of a test tube, or the external surface of a rod. Alternatively, the surface can be flat, such as a sheet, culture dish, test strip, etc. For example, supports may include polystyrene beads. Those skilled in the art will know many other suitable carriers for binding antibody, peptide or antigen, or can ascertain the same by routine experimentation.

Well known method steps can determine binding activity of a given lot of anti-CPAA peptide and/or antibody. Those skilled in the art can determine operative and optimal assay conditions by routine experimentation.

Detectably labeling a CPAA-specific peptide and/or antibody can be accomplished by linking to an enzyme for use in an enzyme immunoassay (EIA), or enzyme-linked immunosorbant assay (ELISA). The linked enzyme reacts with the exposed substrate to generate a chemical moiety which can be detected, for example, by spectrophotometric, fluorometric or by visual means. Enzymes which can be used to detectably label the CPAA-specific antibodies of the present invention include, but are not limited to, malate dehydrogenase, staphylococcal nuclease, delta-5-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase.

By radioactively labeling the CPAA-specific antibodies, it is possible to detect CPAA through the use of a radioimmunoassay (RIA). See Work et al., LAB. TECHNIQUES & BIOCHEM. IN MOLEC. BIO. (No. Holland Pub. Co., NY, 1978). The radioactive isotope can be detected by such means as the use of a gamma counter or a scintillation counter or by autoradiography. Isotopes which are particularly useful for the purpose of the present invention include: $^3$H, $^{125}$I, $^{131}$I, $^{35}$S, $^{14}$C, and $^{125}$I.

It is also possible to label the CPAA-specific antibodies with a fluorescent compound. When the fluorescent labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The CPAA-specific antibodies can also be detectably labeled using fluorescence-emitting metals such as $^{125}$Eu, or others of the lanthanide series. These metals can be attached to the CPAA-specific antibody using such metal chelating groups as diethylenetriaminepentaacetic acid (DTPA) or ethylenediamine-tetraacetic acid (EDTA).

The CPAA-specific antibodies also can be detectably labeled by coupling to a chemiluminescent compound. The presence of the chemiluminescently labeled antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound can be used to label the CPAA-specific antibody, portion, fragment, polypeptide, or derivative of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Detection of the CPAA-specific antibody, portion, fragment, polypeptide, or derivative can be accomplished by a scintillation counter, for example, if the detectable label is a radioactive gamma emitter, or by a fluorometer, for example, if the label is a fluorescent material. In the case of an enzyme label, the detection can be accomplished by colorometric methods which employ a substrate for the enzyme. Detection can also be accomplished by visual comparison of the extent of enzymatic reaction of a substrate in comparison with similarly prepared standards.

For the purposes of the present invention, the CPAA which is detected by the above assays can be present in a biological sample. Any sample containing CPAA may be used. For example, the sample is a biological fluid such as, for example, blood, serum, lymph, urine, feces, inflammatory exudate, cerebrospinal fluid, amniotic fluid, a tissue extract or homogenate, and the like. The invention is not limited to assays using only these samples, however, it being possible for one of ordinary skill in the art, in light of the present specification, to determine suitable conditions which allow the use of other samples.

In situ detection can be accomplished by removing a histological specimen from a patient, and providing the combination of labeled antibodies of the present invention to such a specimen. The antibody (or portion thereof) may be provided by applying or by overlaying the labeled antibody (or portion) to a biological sample. Through the use of such a procedure, it is possible to determine not only the presence of CPAA but also the distribution of CPAA in the examined tissue. Using the present invention, those of ordinary skill will readily perceive that any of a wide variety of histological methods (such as staining procedures) can be modified in order to achieve such in situ detection.

The antibody, fragment or derivative of the present invention can be adapted for utilization in an immunometric assay, also known as a "two-site" or "sandwich" assay. In a typical immunometric assay, a quantity of unlabeled antibody (or fragment of antibody) is bound to a solid support that is insoluble in the fluid being tested and a quantity of detectably labeled soluble antibody is added to permit detection and/or quantification of the ternary complex formed between solid-phase antibody, antigen, and labeled antibody.

Typical, immunometric assays include "forward" assays in which the antibody bound to the solid phase is first contacted with the sample being tested to extract the CPAA from the sample by formation of a binary solid phase antibody-CPAA complex. After a suitable incubation period, the solid support is washed to remove the residue of the fluid sample, including unreacted CPAA, if any, and then contacted with the solution containing a known quantity of labeled antibody (which functions as a "reporter molecule"). After a second incubation period to permit the labeled antibody to complex with the CPAA bound to the solid support through the unlabeled antibody, the solid support is washed a second time to remove the unreacted labeled antibody. This type of forward sandwich assay can be a simple "yes/no" assay to determine whether CPAA is present or can be made quantitative by comparing the measure of labeled antibody with that obtained for a standard sample containing known quantities of CPAA. Such "two-site" or "sandwich" assays are described by Wide, in RADIOIMMUNE ASSAY METHODS 199 (Kirkham, ed., Livingstone, Edinburgh, 1970).

Other types of "sandwich" assays, which can also be useful with CPAA, are the so-called "simultaneous" and "reverse" assays. A simultaneous assay involves a single incubation step wherein the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period, is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays. In one embodiment, a combination of antibodies of the present invention specific for separate epitopes can be used to construct a sensitive three-site immunoradiometric assay.

Additionally, the exemplary antibodies can be utilized for T-cell typing, for isolating specific CPAA-bearing cells or fragments, for vaccine preparation, or the like. The antibodies may be used to quantitatively or qualitatively detect the CPAA in a sample or to detect presence of cells that express the CPAA. This can be accomplished by immunofluorescence techniques employing a fluorescently labeled antibody (see below) coupled with fluorescence microscopy, flow cytometric, or fluorometric detection. For diagnostic purposes, the antibodies may either be labeled or unlabeled. Unlabeled antibodies can be used in combination with other labeled antibodies (second antibodies) that are reactive with the humanized antibody, such as antibodies specific for human immunoglobulin constant regions. Alternatively, the antibodies can be directly labeled. A wide variety of labels may be employed, such as radionuclides, fluors, enzymes, enzyme substrates, enzyme cofactors, enzyme inhibitors, ligands (particularly haptens), etc. Numerous types of immunoassays, such as those discussed previously are available and are well known to those skilled in the art.

The antibodies useful in the present invention may be employed histologically, as in immunofluorescence or immunoelectron microscopy, for in situ detection of the CPAA of the present invention. In situ detection may be accomplished by removing a histological specimen from a patient, and providing the labeled antibody of the present invention to such a specimen. The antibody (or fragment) may be provided by applying or by overlaying the labeled antibody (or fragment) to a biological sample. Through the use of such a procedure, it is possible to determine not only the presence of the CPAA but also its distribution on the examined tissue. Using the present invention, those of ordinary skill will readily perceive that any of wide variety of histological methods (such as staining procedures) can be modified in order to achieve such in situ detection.

Importantly, the antibodies of the present invention may be helpful in diagnosing the invasiveness of certain types of colorectal and pancreatic cancer. More specifically, the antibody of the present invention may identify CPAA present in patients with slow cancers that grow over several years as opposed to aggressive cancers that progress much faster. Thus, the antibody of the present invention may provide an important immunohistochemistry tool.

The antibodies of the present invention may be used on antibody arrays, highly suitable for measuring gene expression profiles including post-translational modification and also useful for detecting smaller molecules such as peptide hormones and carbohydrates. Several approaches have recently been employed to determine the suitability and efficacy of antibody arrays. In some instances, phage-displayed antibodies have been used in preparing the arrays, and detection and analysis is done by SELDI (surface-enhanced laser desorption/ionization), or in a high-throughput format by filter-based enzyme-linked immunosorbent assay (ELISA). Other examples of detection systems include fluorescent tags and nanoelectrodes, and for smaller arrays, surface plasmon resonance and MALDI-TOF (matrix-assisted laser desorption ionization-time of flight) mass spectrometry. Proteome analysis can also be performed by first generating an array of bound antigens followed by antibody capture and detection with an affinity ligand such as Protein L or Protein A bound to a detection probe.

A third approach involves high-density gridding of bacteria containing antibody genes onto a filter followed by interaction with another filter containing an affinity ligand or the antigen attached with a detection probe such as ELISA. This method eliminates the need for liquid handling, and parallel screens of tens of thousands of antibodies against multiple antigens can be performed to identify ultimately proteins that are differentially expressed. A final method involves the possibility of synthesizing antibodies directly on the chip using combinatorial chemistry. Current technology, however, somewhat strained at synthesizing even the antigen-binding antibody domains that consists of a minimum of 120 aminoacids, unless presynthesized polypeptide building blocks are used to create an antibody framework followed by the addition of individual amino acids.

Screening methods for determining anti-CPAA activities are also provided for in the present invention. Specifically, as described further in Example 6, the antibody of the present invention is associated with antibody-dependent cellular cytotoxicity (ADCC) activity. Anti-CPAA compounds that can be selected from the group consisting of antibodies, or fragments or portions thereof, peptides, peptido mimetic compounds or organo mimetic compounds that trigger death of CPAA-bearing cells in vitro, in situ or in vivo are encompassed by the present invention. Screening methods which can be used to determine ADCC activity of an anti-CPAA compound can include in vitro or in vivo assays. Such in vitro assays can include a CPAA cytotoxicity assay, such as a radioimmuno assay, which determines a decrease in cell death by contact with CPAA, such as chimpanzee or human CPAA in isolated or recombinant form, wherein the concurrent presence of a CPAA neutralizing compound reduces the degree or rate of cell death.

Diagnostic Kits

Kits can also be supplied for use with the subject antibodies in the protection against or detection of a cellular activity or for the presence of a selected antigen. Thus, an antibody of the present invention may be provided, usually in a lyophilized form in a container, either alone or in conjunction with additional antibodies specific for the desired cell type. The antibodies, which may be conjugated to a label or toxin, or unconjugated, are included in the kits with buffers, such as Tris, phosphate, carbonate, etc., stabilizers, biocides, inert proteins, e.g., serum albumin, or the like. Generally, these materials will be present in less than 5% wt. based on the amount of active antibody, and usually present in total amount of at least about 0.001% wt. based again on the antibody concentration. Frequently, it will be desirable to include an inert extender or excipient to dilute the active ingredients, where the excipient may be present in from about 1% to 99% wt. of the total composition. Where a second antibody capable of binding to the primary antibody is employed in an assay, this will usually be present in a separate vial. The second antibody is typically conjugated to a label and formulated in an analogous manner with the antibody formulations described above. The kit will generally also include a set of instructions for use.

Pharmaceutical Applications

The anti-CPAA antibodies or peptides of the present invention can be used for example in the treatment of carcinomas and related conditions. More specifically, the invention further provides for a pharmaceutical composition comprising a pharmaceutically acceptable carrier or diluent and, as active ingredient, an antibody or peptide according to the invention. The delivery component of the immunotoxin is a humanized antibody according to the present invention. Intact immunoglobulins or their binding fragments, such as Fab, are also envisioned. Typically, the antibodies in the immunotoxins will be of the human IgA, IgM or IgG isotype, but other mammalian constant regions may be utilized as desired. The composition may also comprise an immunotoxin according to the invention. The humanized antibody, immunotoxin and pharmaceutical compositions thereof of this invention are useful for parenteral administration, e.g., subcutaneously, intramuscularly or intravenously.

Anti-CPAA antibodies and/or peptides of the present invention can be administered either as individual therapeutic agents or in combination with other therapeutic agents. They can be administered alone, but are generally administered with a pharmaceutical carrier selected on the basis of the chosen route of administration and standard pharmaceutical practice.

For parenteral administration, anti-CPAA antibodies or peptides can be formulated as a solution, suspension, emulsion or lyophilized powder in association with a pharmaceutically acceptable parenteral vehicle. For example the vehicle may be a solution of the antibody or a cocktail thereof dissolved in an acceptable carrier, such as an aqueous carrier such vehicles are water, saline, Ringer's solution, dextrose solution, or 5% human serum albumin, 0.4% saline, 0.3% glycine and the like. Liposomes and nonaqueous vehicles such as fixed oils can also be used. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjustment agents and the like, for example sodium acetate, sodium chloride, potassium chloride, calcium chloride, sodium lactate, etc. The concentration of antibody in these formulations can vary widely, for example from less than about 0.5%, usually at or at least about 1% to as much as 15% or 20% by weight and will be selected primarily based on fluid volumes, viscosities, etc., in accordance with the particular mode of administration selected. The vehicle or lyophilized powder can contain additives that maintain isotonicity (e.g., sodium chloride, mannitol) and chemical stability (e.g., buffers and preservatives). The formulation is sterilized by commonly used techniques.

Thus, a typical pharmaceutical composition for intramuscular injection could be made up to contain 1 ml sterile buffered water, and 50 mg of antibody. A typical composition for intravenous infusion could be made up to contain 250 ml of sterile Ringer's solution, and 150 mg of antibody. Actual methods for preparing parenterally administrable compositions will be known or apparent to those skilled in the art and are described in more detail in, for example, REMINGTON'S PHARMA. SCI. (15th ed., Mack Pub. Co., Easton, Pa., 1980).

The antibodies of this invention can be lyophilized for storage and reconstituted in a suitable carrier prior to use. This technique has been shown to be effective with conventional immune globulins. Any suitable lyophilization and reconstitution techniques can be employed. It will be appreciated by those skilled in the art that lyophilization and reconstitution can lead to varying degrees of antibody activity loss (e.g., with conventional immune globulins, IgM antibodies tend to have greater activity loss than IgG antibodies) and that use levels may have to be adjusted to compensate.

The compositions containing the present human-like antibodies or a cocktail thereof can be administered for prevention of recurrence and/or therapeutic treatments for existing disease. Suitable pharmaceutical carriers are described in the most recent edition of REMINGTON'S PHARMACEUTICAL SCIENCES, a standard reference text in this field of art. For example, a parenteral composition suitable for administration by injection is prepared by dissolving 1.5% by weight of active ingredient in 0.9% sodium chloride solution. Anti-CPAA peptides and/or antibodies of this invention can be adapted for therapeutic efficacy by virtue of their ability to mediate antibody-dependent cellular cytotoxicity (ADCC), and/or apoptosis, and/or complement-dependent cytotoxicity (CDC) against cells having CPAA associated with their surface. For these activities, either an endogenous source or an exogenous source of effector cells (for ADCC) or complement components (for CDC) can be utilized.

In therapeutic application, compositions are administered to a patient already suffering from a disease, in an amount sufficient to cure or at least partially arrest or alleviate the disease and its complications. An amount adequate to accomplish this is defined as a "therapeutically effective dose." Amounts effective for this use will depend upon the severity of the malignancy and the general state of the patient's own immune system, but generally range from about 1 mg to about 200 mg of antibody per dose, with dosages of from 5 mg to 25 mg per patient being more commonly used. It must be kept in mind that the materials of the invention may generally be employed in serious disease states, often life-threatening or potentially life-threatening situations. In such cases, in view of the minimization of extraneous substances and the lower probability of "foreign substance" rejections which are achieved by the present human-like antibodies of this invention, it is possible and may be felt desirable by the treating physician to administer substantial excesses of these antibodies.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily, weekly, or biweekly dosage of active ingredient can be about 100 mg/m$^2$ to 250 mg/m$^2$ of body weight delivered over a 4 hour to 6 hour period.

As a non-limiting example, treatment of CPAA-related pathologies humans or animals can be provided as a daily, weekly, or biweekly dosage of anti-CPAA peptides, monoclonal chimeric and/or murine antibodies of the present invention in a dosage range from 0.1 mg/kg to 100 mg/kg, per day, weekly, or biweekly.

Example antibodies for human therapeutic use are high affinity (these may also be high avidity) murine and chimeric antibodies, and fragments, regions and derivatives having potent in vivo anti-CPAA activity, according to the present invention.

Dosage forms (composition) suitable for internal administration generally contain from about 0.1 mg to about 500 mg of active ingredient per unit. In these pharmaceutical compositions the active ingredient will ordinarily be present in an amount of about 0.5%-95% by weight based on the total weight of the composition.

Single or multiple administrations of the compositions can be carried out with dose levels and pattern being selected by the treating physician. In any event, the pharmaceutical formulations should provide a quantity of the antibody(ies) of this invention sufficient to effectively treat the patient.

The antibodies can also be used as separately administered compositions given in conjunction with chemotherapeutic or immunosuppressive agents. Typically, the agents will include cyclosporin A or a purine analog (e.g., methotrexate, 6-mercaptopurine, or the like), but numerous additional agents (e.g., cyclophosphamide, prednisone, etc.) well-known to those skilled in the art may also be utilized.

An antibody of the present invention may form part of an immunotoxin. Immunotoxins are characterized by two components and are useful for killing selected cells in vitro or in vivo. One component is a cytotoxic agent which is usually fatal to a cell when attached or absorbed. The second component, known as the "delivery vehicle", provides a means for delivering the toxic agent to a particular cell type, such as cells comprising a carcinoma. The two components are commonly chemically bonded together by any of a variety of well-known chemical procedures. For example, when the cytotoxic agent is a protein and the second component is an intact immunoglobulin, the linkage may be by way of heterobifunctional cross-linkers, e.g., SPDP, carbodiimide, glutaraldehyde, or the like. Production of various immunotoxins is well-known with the art, and can be found, for example in Thorpe et al., *Monoclonal Antibody*-Toxin *Conjugates: Aiming the Magic Bullet, in* MONOCLONAL ANTIBODIES IN CLIN. MED. 168 (Acad. Press. 1982).

A variety of cytotoxic agents are suitable for use in immunotoxins. Cytotoxic drugs interfere with critical cellular processes including DNA, RNA, and protein synthesis. Cytotoxic agents can include radionuclides, such as include $^{212}$Bi, $^{131}$I, $^{188}$Re, and $^{90}$Y; a number of chemotherapeutic drugs, such as vindesine, methotrexate, adriamycin, and cisplatin; and cytotoxic proteins such as ribosomal inhibiting proteins like pokeweed antiviral protein, *Pseudomonas* exotoxin A, ricin, *diphtheria* toxin, ricin A chain, etc., or an agent active at the cell surface, such as the phospholipase enzymes (e.g., phospholipase C). See generally, Olsnes & Phil, *Chimeric Toxins,* 25 Pharmac. Ther. 335 (1982); MONOCLONAL ANTIBODIES FOR CANCER DETECTION & THERAPY, 159, 224 (Baldwin & Byers eds., Acad. Press, 1985).

The antibodies or peptides and derivatives can be used therapeutically as immunoconjugates. See Dillman, 111 Ann. Internal Med. 592 (1989). Such antibodies or polypeptides can be coupled to cytotoxic proteins, including, but not limited to ricin-A, *Pseudomonas* toxin and *Diphtheria* toxin. Toxins conjugated to antibodies or other ligands or peptides are well known in the art. See, e.g., Olsnes et al., 10 Immunol. Today 291 (1989). Plant and bacterial toxins typically kill cells by disrupting the protein synthetic machinery. Cytotoxic drugs that can be conjugated to anti-CPAA peptides and/or antibodies and subsequently used for in vivo therapy include, but are not limited to, daunorubicin, doxorubicin, methotrexate, and Mitomycin C. For a description of these classes of drugs which are well known in the art, and their mechanisms of action, see Goodman & Gilman's PHARMACOLOGICAL BASIS OF THERAPEUTICS (8th Ed., Macmillan Pub. Co., 1990).

Additionally, the antibody of the present invention may be delivered in combination with chemotherapeutic agents such as oxaliplatin, irinotecan, topotecan, leucovorin, carmustine, vincristine, fluorouracil, streptozocin, and gemcitabine. Combinations of other antibodies and such compounds have been used in advanced colorectal cancer patients. See, e.g., U.S. Patent Application Pub. No. 2002/0187144.

Anti-CPAA antibodies and/or peptides of this invention can be advantageously utilized in combination with other monoclonal or murine and chimeric antibodies, fragments and regions, or with lymphokines or hemopoietic growth factors, etc., which serve to increase the number or activity of effector cells which interact with the antibodies. For example, the antibody of the present invention may be co-administered with human monoclonal antibodies reactive with other markers on cells responsible for the disease. For example, suitable T-cell markers can include those grouped into the so-called "Clusters of Differentiation" as named by the First International Leukocyte Differentiation Workshop, in LEUKOCYTE TYPING (Bernard et al., eds., Springer-Verlag, NY, 1984).

The 16C3 Antigen

The antigen to which the 16C3 antibody binds appears to be expressed in some, but not all, cultured human tumor cell lines, in some but not all normal human embryonic gut tissues, and in most colon and pancreas tumor tissues. As detailed in the Examples, below, upon western blotting of various tumor samples, the 16C3 antibody recognized both a ~200 kDa peptide species and a ~110 kDa peptide species. The intensity of the staining, which may reflect the amount of each protein species from a particular sample, appears to differ between colorectal tumor samples and pancreatic tumor samples. The 16C3 antigen appears to be expressed in most colon and pancreas tumor tissues, and may have an oncofetal origin. The 16C3 antigen is expressed on the cell surface and is a glycoprotein. There may be two related species of the same antigen that the 16C3 antibody recognizes, and the relative amount of each species differs between colon and pancreas tumor tissues.

Binding of the 16C3 antigen by western blotting is not disrupted by treatment with either detergents such as SDS and NP-40, or reducing agents such as dithiothreitol and 2-mercaptoethanol; suggesting that binding to the specific epitope is not conformation-dependent, and that 16C3 antibody may recognize a linear epitope on the CPAA. Furthermore, the 16C3 epitope is unaffected by treatment with V8 protease, trypsin or PNGase-F, although the overall migration of the immunoreactive antigen on SDS-PAGE was changed, reflecting modification by proteolysis and deglycosylation. Treatment with sodium hydroxide in a beta-elimination chemical reaction appeared to result in a loss of immunoreactivity, suggesting that the 16C3 epitope may involve an O-linked glycosylation modification, or lie adjacent to an O-linked glycosylation residue. Further studies define the precise epitope to which the 16C3 antibody reacts.

The characterization of the 16C3 epitope may also lead to the identification of the gene(s) for the CPAA, such as that it may provide a target for translation antagonists or other means of blocking expression, or an understanding of the CPAA activity such that it may become a target for antagonists, particularly small molecules or antibodies, which block functional activity (such as, for example, binding of the receptor by its cognate ligand(s); transport function; signaling function).

Cancer Vaccine

Another aspect of the present invention provides for a cancer vaccine. By "vaccine" is meant an agent used to stimulate the immune system of a living organism. In this regard, the immune response may provide for prophylaxis or may provide for a positive effect in a diseased organism by, for example, alleviating an existing condition. Specifically, a cancer vaccine is meant to therapeutically treat existing malignancy and/or to prevent the progression or metastasis of an existing malignancy.

That specific active immunotherapy can be achieved using tumor-associated antigens is widely known. Indeed, the initial, semi-purified antigenic preparations used to derive the monoclonal antibody that has allowed the further invention presented herein were shown to provide specific, active, long-lasting protective immunity in humans. Hollinshead et al., 1985. At that time, patients had undergone tumor resection and were then vaccinated with antigenic material derived from tumor membranes in the amount of 200 µg, 300 µg, or 500 µg in 0.2 ml dispersions mixed with an additional 0.2 ml Freund's adjuvant. Dosages of 300 µg given monthly for three months were shown to be safe.

With the recombinant antibodies described herein, it is now possible to define a highly purified antigen or epitope peptides of CPAA that is further suitable for a vaccine against these cancers. For example, 16C3 may be used to bind to tissue or cell samples from which the CPAA protein and its corresponding amino acid sequence may be identified by any number of known techniques. The epitope may be mapped further, and the molecular nature determined with exquisite detail. See, e.g, Baerga-Oritz et al., 11 Protein Sci. 1300 (2002); Jemmerson, & Paterson, 4 BioTechniques 18 (1986).

An alternative technique to identify effective antigenic peptides entails using the 16C3 antibody or peptide to screen an expression library (such as a phage display library) for mimetic proteins, or mimotopes, that are recognized by the antibody. This technique has been used to identify antigenic peptides that have raised protective immune responses in vivo. See Beenhouwer et al., 169 J. Immunol. 6992 (2002); see also U.S. Pat. No. 5,837,550; Visvanathan et al., 48 Arthritis & Rheumatism, 737 (2003); Sato et al., 371 Biochem. J. 603 (2003). Note that this technique has been used to identify protein mimetics of carbohydrate and glycoprotein antigens, the protein versions found to be more immunogenic than the natural carbohydrate counterparts. Indeed, mimetics may be isolated that are advantageous over known antigens because of factors including production capacity, safety, half-life, or other issues.

The CPAA immunogenic protein may be prepared and delivered, for example, as either a subcutaneous or a mucosal vaccine alone, or associated with an adjuvant or carrier or as part of an adjuvant or protein conjugate. Delivery by liposomes microparticles, virus-like particles, DNA vaccines, live recombinant vectors such as *S. typhimurium*, and possibly ISCOMs are envisioned. All of these systems are well-known by those of ordinary skill in the art, and may be practiced without undue experimentation. See, e.g., Michalek et al., in MUCOSAL IMMUNOLOGY (Mestecky et al., eds., Elsevier, 2005).

Additionally, the CPAA peptide may be genetically or chemically conjugated to a toxoid carrier, such as cholera, entero-, or ricin toxoid. See, e.g., U.S. Pat. No. 6,846,488. Another advantageous protein carrier derived from bacterium is the PorB protein carrier. See e.g., U.S. Pat. No. 6,613,336. Another promising protein-based mucosal adjuvant is the flagellin protein from *S. typhimurium*. In an embodiment of the invention, the CPAA protein is co-administered with the flagellin protein (FljB) via, for example, the mucosal intranasal route. An advantageous protein platform comprising duck hepatitis core antigen is also presented in U.S. Patent Application Pub. No. 2004/0219164.

The CPAA of the present invention may also be delivered as a DNA vaccine for in vivo expression of the immunogenic construct. For example, cationic microparticles may be used to deliver the DNA expression cassette in intranasal vaccination. Such systems have induced an immune response following, for example, intranasal delivery of vaccine comprising DNA encoding the HIV-1 gag protein. Michalek et al., 2005. In an embodiment of the present invention, the CPAA immunogenic peptide is delivered via a DNA expression cassette which is subsequently expressed in vivo.

Additionally, the immunogenic preparation may be used to "charge" donor derived dendritic cells ex vivo, which are then returned to the patient where they home to the lymphoid organs and mount an effective immune response. See, e.g., Liau et al., 9 Neurosurg. Focus, e8 (2000); Baar, 4(2) Oncologist 140 (1999). This vaccine approach has been in human trials for treating, for example, melanoma and brain cancer. More information may be found on-line at, for example, the National Institutes of Health's web site for clinical trials. Alternatively, a DNA vaccine as described above may be delivered via skin patch to the cells of Langerhans, which then mature to dendritic cells and home to the lymphoid organs. U.S. Pat. No. 6,420,176.

Delivery of the immunogenic compositions of the present invention may be by parenteral, subcutaneous, or intramuscular injection, intravenous injection, intestinal, intradermal, intubation, or nasal, oral or rectal vaccination. The vaccine may also be delivered topically, including intranasal, upon the palatine tonsil, or delivery to the salivary glands. In other words, a vaccine contemplated by the present invention may be administered to the patient by any known or standard techniques.

The invention will now be described further by non-limiting examples.

EXAMPLES

Example 1. Preparation of Pancreatic and Colorectal Carcinoma-Associated Antigen (CPAA) from Human Tumor Specimens An immunogenic tumor associated antigen preparation was obtained from pooled colorectal carcinoma membranes according to the method described by Hollinshead et al., 56 Cancer 480 (1985); U.S. Pat. No. 5,688,657. This antigenic material was purified to the extent that the membrane fractions were free of HL-A antigens and were separated from much of the non-immunogenic glycoprotein fractions.

Tumor cell suspensions in saline were prepared from fresh operating room specimens. Single cell suspensions, obtained by mincing solid tumors, were centrifuged for 10 min. at 400× gravity and the supernatant was retained. The cell pellet was resuspended in phosphate buffered saline (PBS) and re-centrifuged. The membrane material was examined by electron microscopy to assure that only membrane material (and no intact cells) was present, and the protein content was measured by the Lowry method. The membrane material was next subjected to sequential low frequency sonication and resuspended as a soluble pool of membrane proteins. The soluble sonicates were separated by gel filtration on Sephadex-6200. Fractions of 2 ml were collected and the absorbance profile at 220 nm and 280 nm was recorded. Fractions comprising individual protein peaks were pooled, and the pools were concentrated by Diaflo ultrafiltration. Sephadex-G200 fractions IB and IIA, as defined by Hollinshead et al., 1985, were further purified by gradient polyacrylamide gel electrophoresis (PAGE). The fractions were tested for their ability to elicit positive delayed cutaneous hypersensitivity reactions in patients with colorectal carcinoma. Those fractions with immunogenic activity were said to contain colorectal carcinoma-associated antigens and were employed as immunogens and screening agents in the preparation of monoclonal antibodies.

By gradient PAGE, a double-banded antigen distinct from that of carcinoembryonic antigen was identified and isolated. Gold et al., 122 J. Exp. Med. 467 (1965); Hollinshead et al., 1985; Hollinshead et al., 1(7658) Lancet 1191 (1970); Hollinshead et al., 177 Science 887 (1972). The bands comprising this antigen migrated 6.3 cm and 6.6 cm distant from tracking dye. Biochemical analysis of the antigen indicated that this protein was a glycoprotein. The molecular weight of the antigen was estimated based on the electrophoretic mobility of transferrin (6.4 cm-6.5 cm), one isolate has a molecular weight of 76.5 kDa. The semi-purified antigens were studied in detail, including assessments of serum antibodies, cell-mediated immunity, and patient survival. Hollinshead et al., Abstract, Ann. Meeting Am. Soc. Clin. Oncol., Washington, D.C. (1990); Hollinhead et al., 56 Proc. 6th Intl. Conf. Adjuvant Therapy Cancer (Salmon, ed., W.B. Saunders Inc., Philadelphia, Pa., 1990). Additional studies were performed to evaluate the usage of combination immuno-chemotherapies. Hollinshead et al., 1990a; Hollinshead et al., 1990b; Hollinshead, 7 Sein. Surg. Oncol. 199 (1991); Hollinshead et al., 10(1) J. Exper. Clin. Cancer 43 (1991); see also Hollinshead & Herberman, Proc. 2nd Intl. Symp. Cancer Detection & Prevent. 616 (Bologna, Italy, 1973); Hollinshead, *Experience with combo. immuno-chemotherapy of colon cancer: steps pertinent to successful therapy based upon dosage & timing of admin. of 5-FU.* NIH Workshop on Levamasole: Mechanism of anti-tumor action (Bethesda, Md., Jun. 11, 1990); Hollinshead, 7 Semin. Surg. Oncol., 199 (1991); Hollinshead, 8 Clin. Exper. Metastasis 89 (1990).

Example 2. Immunization and Preparation of Hybridomas

Monoclonal antibodies against human pancreatic and colorectal carcinoma-associated antigens were obtained by the production and cloning of hybrids resulting from the fusion of mouse myeloma cells Sp2/0-Ag14 with spleen cells from BALB/c mice which had been immunized with the CPAA described above. Hybrid clones were established and reacted strongly with the CPAA and with a colon carcinoma cell line (LS174T) when assayed by ELISA.

Immunization and Cell Fusion: BALB/c mice were immunized by intraperitoneal injection of 100 μg of the CPAA emulsified in complete Freund's adjuvant. The CPAA was prepared as described by Hollinshead in clinical trials. Four weeks later, a second immunization with 50 μg of CPAA emulsified in incomplete Freund's adjuvant was performed. Fourteen days later the mice received an intraperitoneal booster injection of 50 μg of CPAA emulsified in incomplete Freund's adjuvant. Mice were sacrificed three days later and a single cell splenocyte suspension was prepared. Cell fusion was performed by incubation of 5e7 mouse spleen cells with 10e7 sP2/0-Ag14 myeloma cells in 40% polyethylene glycol (MW=1500).

Screening of Hybridoma Clones: An enzyme-linked immunosorbent assay (ELISA) was used to detect hybridoma clones producing antibodies specific for the PCAA. Colon tumor cell membrane extract (10 ng/well of LS174T or HT-29) served as a surrogate source of colon cancer antigens and was immobilized on polystyrene microplates. Antibodies present in the test supernatants were allowed to bind to the immobilized antigens for one hour. The presence of the bound murine mAbs was detected with phosphatase-conjugated secondary antibodies, specific for mouse immunoglobulin. Wells were washed and then the chromogenic substrate for alkaline phosphatase (pNPP) was added. Wells showing color reactions yielding absorbances greater or equal to 0.500 units were scored as positive. Negative controls gave values of 0.01 to 0.09 absorbance units. Hybridoma wells scoring as positive by ELISA were selected for expansion and repeating the cell cloning procedure by the limiting dilution cloning method. Selection of positive mAb producing hybridoma cells was determined by ELISA. Positive monoclonal cells were expanded in culture and aliquots of the cells were frozen under liquid nitrogen for long term storage.

Example 3. Isotype of the 16C3 mAb

Murine immunoglobulins are expressed from separate genes that encode the heavy chain (55 kD) and the light chain (25 kD-29 kD). There are four heavy chains of the IgG subclass (IgG1, IgG2a, IgG2b, IgG3) and two light chains (Kappa, Lambda) that can rearrange to yield the repertoire of murine immunoglobulins.

The isotype of the 16C3 mAb was determined using the Southern Biotechnology, Inc. mouse isotyping kit. The 16C3 mAb was determined to be an IgG1 heavy chain and a Kappa light chain.

Example 4. Unique DNA Sequences Encode the 16C3 Antibody

The linear amino acid sequence of a mAb identifies its uniqueness, in comparison to the known sequences of all other mAbs described. The linear amino acid sequence can be determined by first determining the linear sequence of the DNA that encodes the polypeptide molecule. The DNA sequence that encodes the 16C3 mAb was determined and the open reading frame was translated into the amino acid sequence using the universal mammalian codon usage table, thus describing the linear sequence identity of the 16C3 molecule.

Oligonucleotide primers used for the murine IgG1 heavy chain kappa light chain cloning derived from the publication *Rapid cloning of any rearranged mouse immunoglobulin variable genes*, Dattamajumdar et al., 43 Immunogenetics 141 (1996).

Isolation of the nucleic acid of 16C3: Ribonucleic acid (RNA) was isolated from the 16C3-producing hybridoma cells using the RNeasy-Midi kit (catalog #74104, Qiagen, Valencia, Calif.) as described by the manufacturer. Four million cells were centrifuged in a conical tube, and the cells were lysed to release the nuclear and cytosolic nucleic acids including the RNA. The RNA was then purified from the lysate using the RNeasy spin columns. Finally, the RNA was eluted with water and analyzed for yield and purity by absorbance at 260 nm and 280 nm using a spectrophotometer. The isolated RNA was stored at −80° C.

Preparation of the cDNA: The RNA (2 µg) was first reverse-transcribed to cDNA using a deoxynucleotide triphosphate dNTP mixture (dATP, dCTP, dGTP, dTTP), cDNA synthesis buffer, RNase inhibitor, reverse transcriptase enzyme, and oligo(dT)$_{20}$. The cDNA synthesis reaction was performed according to the manufacturer's instructions in Invitrogen's Superscript III kit (catalog #18080-051). The target cDNA (mouse IgG1 heavy chain and Kappa light chain) were amplified for sequencing purposes by the polymerase chain reaction (PCR) following the instructions recommended by the Accuprime Pfx DNA polymerase kit from Invitrogen (catalog #12344-024) using the forward and reverse primers described above for both the heavy chain and light chain. The mixture was subjected to 94° C. for 2 min., followed by thirty cycles of: 15 sec. at 94° C., 30 sec. at 58° C., 30 sec. at 68° C. which was then followed by 10 min. at 68° C. The amplified heavy and light chain DNA fragments were then electrophoresed on a 4% NuSieve 3:1 plus agarose gel (Lonza-Rockland, catalog #54925). The target DNA bands were excised from the gel and then purified from the agarose using QIAquick gel extraction kit (catalog #28704, Qiagen).

DNA sequencing and analysis: Amplified target DNA representing the variable regions of the heavy chain and light chain of 16C3 antibody was TOPO cloned for sequencing according to the manufacturers instructions (Invitrogen catalog #K4530-20). Several TOPO clones were selected and subjected to DNA sequencing. Full-length sequences for the 16C3 antibody were obtained using the 5'/3' RACE kit according to the manufacturer's instructions (Roche Applied Sci., catalog #03-353). The DNA sequences obtained were translated in three reading frames and the frame without stop codons and that aligned homologously with other murine heavy and light chains was determined to be the genuine reading frame. The DNA sequence was used as the query sequence to search the National Center for Biotechnology Information (NCBI) database (All GenBank+RefSeq Nucleotides+EMBL+DDBJ+PDB sequences). The BLAST search returned up to fifteen database entries with nucleotide sequence similarity to the query sequence of 16C3. None of the DNA sequences were identical to the 16C3 DNA sequence, demonstrating the uniqueness of the 16C3 mAb described herein.

Example 5. Uniqueness of the 16C3 Antibody Confirmed by BLAST Database Search

The sequences of the 16C3 mAb were subjected to BLAST searching (Basic Local Alignment Search Tool) against the protein and nucleic acid database at the National Center for Biotechnology Information (NCBI), part of the National Institutes of Health's National Library of Medicine. Examination of the similar sequences found by this BLAST search with either 16C3 mAb heavy chain or 16C3 mAb light chain query sequences indicated that both the 16C3 mAb heavy chain and light chain variable regions are unique sequences. Thus, the 16C3 mAb heavy and light chain sequences represent a novel and unique antibody molecule.

Example 6. Specific Cell Binding of 16C3 mAb

The 16C3 mAb produced by the hybridoma was purified by affinity chromatography using protein L-agarose matrix. The purified 16C3 mAb was characterized by indirect immunofluorescence, using various tumor cells as identified in Table 1, below. All of the tumor cell lines were obtained from the ATCC. Cells were incubated with purified 16C3 mAb diluted in phosphate buffered saline (PBS) for 1 hr at 4° C. The cells were washed and incubated with a fluorescein-labelled goat anti-mouse mAb. The cells were then washed three times with PBS and examined by flow cytometry using a Becton-Dickinson FACSCalibur™ and CellQuest analysis software. The results appear in Table 1 (FACS data). The data demonstrate the specific binding of 16C3 mAb to colorectal and pancreatic tumor cell lines, but not to prostate or squamous tumor cell lines.

TABLE 1

16C3 mAb FACS data: binding to tumor cell lines

| Tumor Cell Line | % Cell Staining (mfi) | |
|---|---|---|
| | FITC-Ab only | Rockland 16C3-E12 |
| LS174T Colorectal | 0.94 (15) | 40.56 (59) |
| HT-29 Colorectal | 0.84 (10) | 90.99 (78) |
| CFPAC-1 Pancreatic | 0.83 (14) | 96.19 (323) |
| AsPC-1 Pancreatic | 2.68 (30) | 69.90 (36) |
| 22Rv-1 Prostate | 2.74 (61) | 1.62 (30) |
| PC-3 Prostate | 0.28 (20) | 2.44 (22) |
| H226 Squamous | 0.90 (18) | 0.62 (14) |
| SiHa Squamous | 1.07 (19) | 1.08 (20) |

Example 6. ADCC Activity of 16C3 Demonstrating Anti-Tumor Cytotoxicity

A therapeutically useful mAb, specific for an immunogenic tumor antigen, may have at least one of the following properties: (a) high tumor tissue specificity, (b) absence of cross-reactivity to normal human tissue, and (c) a biological activity associated with destruction of tumors, such as antibody-dependent cellular cytotoxicity (ADCC). The ADCC activity of the 16C3 mAb was tested on colon SW1463 and pancreatic CFPAC-1 and AsPC-1 carcinoma lines as target cells. The melanoma cell line, SK-MEL, served as a specificity control. ADCC was assayed using a conventional 4-hour $^{111}$In release assay using normal human PBMC as effector cells, and the results are shown as the percent isotope release (% lysis) in Table 2 (ADCC data). Compared to the negative control antibody, UPC-10, the data indicate a modest killing activity of the murine IgG1 antibody, but, importantly, the killing activity is apparently specific for colon and pancreatic tumor lines. The killing activity of an antibody may increase with humanized or chimerized antibody having human framework sequences that include the Fc region, which interacts with human effector cells in this ADCC assay.

TABLE 2

ADCC assay with murine 16C3 mAb

| Tumor Target | Effector:Target Ratio | % Specific ADCC Activity (±SEM) | |
|---|---|---|---|
| | | 16C3 mAb | UPC-10 |
| SW1463 (colorectal adeno) | 50:1 | 4.1 ± 0.4 | 1.6 ± 0.3 |
| | 25:1 | 5.2 ± 0.3 | −0.2 ± 0.1 |
| CFPAC-1 (pancreas adeno) | 50:1 | 11.1 ± 2.7 | 0.2 ± 0.6 |
| | 25:1 | 1.4 ± 0.7 | −0.2 ± 0.3 |
| AsPC-1 (pancreas adeno) | 50:1 | 16.1 ± 0.8 | 0.9 ± 0.3 |
| | 25:1 | 10.6 ± 1.0 | 0.4 ± 0.2 |
| SK-MEL (melanoma) | 50:1 | −3.0 ± 0.2 | −0.5 ± 0.2 |
| | 25:1 | −3.3 ± 0.1 | −2.0 ± 0.2 |

$^{111}$In labeled target cells, antibodies used at 5 µg/well, IL-2 activated human PBMC used as effector cells, 4 hr incubation at 37° C. before harvest.

Example 7. SDS Polyacrylamide Gel Electrophoresis Analysis of the 16C3 Antibody

The native configuration of murine immunoglobulin gamma (IgG1) is comprised of four polypeptides, with two polypeptides each of a heavy chain and a light chain. One heavy chain (55 kDa) is associated with one light chain (25 kDa-29 kDa) and this dimer is linked to an identical dimer through disulfide bonding to complete the functional tetrameric macromolecule. The IgG molecule can be dissociated into its component heavy and light chains and separated by size on polyacrylamide gel matrix in the presence of denaturing reagent (SDS, sodium dodecyl sulfate) and an agent to reduce the disulfide bridge that links the two heterodimers (DTT, dithiothreitol). Gel electrophoresis is a common analytical method used to define the molecular mass of proteinaceous materials, such as antibodies.

Purified 16C3 mAb was subjected to analysis by SDS polyacrylamide gel electrophoresis in the presence of reducing agent (DTT). Five micrograms of purified 16C3 mAb was mixed with DTT and 4× samples buffer containing SDS, glycerol, and bromophenol blue dye. The mixture was heated to 95° C. for 2 min., cooled on ice, then loaded onto an SDS gradient polyacrylamide gel (4%-20% gradient) and subjected to an electric current to separate the denatured molecular species in the 16C3 mAb preparation. Following electrophoresis, the gel was stained with Coomassie Blue dye to visualize the proteins on the gel, destained with water, and dried between porous plastic sheets. The data demonstrate two protein bands of molecular mass 55 kDa, representing the heavy chain; and 28 kDa, representing the light chain molecular species. These data show that the purified material correspond to the known molecular sizes for murine IgG1 heavy and light chain proteins.

Example 8. Immunohistochemical Staining with 16C3 mAb and Human Malignant Tissues The specificity of antigen binding displayed by the 16C3 mAb was measured by immunohistochemical staining of various human tissue samples, both cancer and normal specimens. Paraffin and fresh frozen human tissue samples were stained with purified mouse 16C3 Mab (IgG1), at 5 µg/mL, then detected using a peroxidase-conjugated anti-mouse IgG secondary antibody. The intensity of staining is indicated in Table 3, reflecting a 0-4 rating system: 0 indicating no cross-reactivity; 4 indicating very high cross-reactivity to the antigen or high expression of the antigen in a given specimen.

TABLE 3

Immunohistochemical staining indicating 16C3 specificity.

| Sample preparation method | number positive/total | stain intensity |
|---|---|---|
| Paraffin-Colon cancer | 31/33 | 3+, 4+ |
| Paraffin-Colon normal | 0/18 | 0 |
| Paraffin-Pancreas cancer | 17/18 | 3+, 4+ |
| Paraffin-Pancreas normal | 0/8 | 0 |
| Paraffin-Colon cancer | 2/2 | 2+, 3+ |
| Paraffin-Lung-adeno cancer | 2/2 | 1+, 2+ |
| Paraffin-Mucinous Ovary cancer | 2/2 | 2+, 3+ |
| Paraffin-Liver-Cholagiocarcinoma | 2/2 | 1+ |
| Paraffin-Stomach cancer | 2/2 | 3+, 4+ |
| Paraffin-Uterus-Cervix cancer | 2/2 | 1+, 2+ |
| Paraffin-Uterus-Endometrial cancer | 0/2 | 0 |
| Paraffin-Prostate cancer | 0/40 | 0 |
| Paraffin-Serous Ovary cancer | 0/2 | 0 |
| Paraffin-Bladder-Transitional cell cancer | 0/2 | 0 |
| Paraffin-Kidney cancer | 0/2 | 0 |
| Paraffin-Lung-squamous cancer | 0/2 | 0 |
| Paraffin-Kidney cancer | 0/2 | 0 |
| Paraffin-Lung-squamous cancer | 0/2 | 0 |
| Paraffin-Esophagus-Squamous | 0/2 | 0 |
| Paraffin-Liver-Hepatoma | 0/2 | 0 |
| Paraffin-Thyroid, papillary | 0/2 | 0 |
| Paraffin-Thyroid, follicular | 0/2 | 0 |
| Paraffin-Breast, ductal | 0/2 | 0 |
| Paraffin-Skin-Squamous | 0/2 | 0 |
| Paraffin-Stomach, signet ring | 0/2 | 0 |
| Paraffin-various normal | 0/54 | 0 |
| Fresh-frozen-Colon cancer | 2/3 | 2+, 3+ |
| Fresh-frozen-Colon normal | 0/2 | 0 |
| Fresh-frozen-Pancreas cancer | 2/3 | 2+, 3+ |
| Fresh-frozen-Pancreas normal | 0/2 | 0 |

Considered collectively, these data demonstrate over 90% binding specificity to colon ($^{35}/_{38}$) and pancreas ($^{19}/_{21}$) cancer tissues, whereas there was no cross-reactivity to any normal human tissues (0 out of 58 tested). There were also some cross-reactivity to other tumor types including lung adenocarcinoma (2/2), mucinous ovarian cancer (2/2), liver cholangiocarcinoma (2/2), stomach cancer (2/2), and uterine-cervix cancer (2/2). These data may indicate a general cross-reactivity with an antigen present on adenocarcinomas.

Example 9. Humanization of Murine 16C3 Monoclonal Antibody

To improve usefulness as a therapeutic drug to treat human malignancy, a mouse monoclonal antibody may be converted to a chimerized or humanized antibody, such that the drug may be administered both repeatedly and with lower toxicity. It is known in the art that administration of a murine protein may sometimes result in massive immune and toxic responses to the foreign protein. Hence, a humanized antibody may prove more efficacious for human therapies.

The humanization of mouse antibodies for therapeutic applications is well known, and several techniques for making humanized mAbs are discussed above. For example, according to the Frankenstein approach, human framework regions are identified as having substantial sequence homology to each framework region of the relevant non-human antibody, and CDRs of the non-human antibody are grafted onto the composite of the different human framework regions. See U.S. Patent Appl. Pub. No. 20060088522. A related method also useful for preparation of antibodies of the invention is described in U.S. Patent Appl. Pub. No. 20030040606.

Five different alternative sequences for converting the murine 16C3 antibody to a humanized, therapeutically useful antibody were designed. The designs were based upon structural information about known murine and human antibody sequences. Each of these variable regions were fused in-frame to a known human IgG1 framework antibody that has been commonly used for other therapeutic antibodies such as CC49 and CC83. The genes were chemically synthesized, the sequences were verified, and then the heavy and light chain gene inserts were cloned into a mammalian expression plasmid under the control of the CMV promoter. It should be noted that the variant light chain designs for VEN16C3 and CDR16C3 are identical so only one light chain gene specified by this sequence design was synthesized. The plasmids encoding each heavy chain and light chain were co-transfected into human 293T cells using standard lipofectamine-based methods and reagents.

The humanized mAb sequences shown in FIG. 6 (light chain sequences) and FIG. 7 (heavy chain sequences) represent potential therapeutic forms of the 16C3 antibody for use in treating human malignancy. Human germline IgG sequences were used for the framework sequences. The abbreviations are as follows: 16C3 is the murine antibody sequence, ven16C3 has been veneered with human framework sequences, cdr16C3 has been remodeled with human CDR amino acids, abb16C3 represents abbreviated CDR grafting, sdr16C3 represents site determining amino acid changes, and fra16C3 represents a "Frankenstein" approach to remodeling the variable region by using a combination of various "pieces" of human variable regions. Numbering is Kabat numbering.

Example 10. Specific Cell Binding of Recombinant Mouse 16C3 mAb

The mouse 16C3 mAb produced by the hybridoma was purified by affinity chromatography using protein L-agarose matrix. Recombinant mouse 16C3 mAb produced by Chinese hamster ovary cells (CHO) was purified by affinity chromatography using protein A-Sepharose matrix. The purified 16C3 preparations, or transfected cell supernatants, were characterized by indirect immunofluorescence using human colorectal LS174T or pancreatic AsPC-1 tumor cells as shown below. Cells were incubated with purified 16C3 (mouse or humanized) diluted in phosphate buffered saline (PBS) for 1 hour at 4° C. The cells were washed and incubated with a fluorescein-labelled goat anti-mouse immunoglobulin antibody. The cells were then washed with PBS and examined by flow cytometry using a Becton-Dickinson FACScalibur and CellQuest analysis software. The data demonstrate very similar binding of both hybridoma-derived and recombinant CHO-derived mouse 16C3 to colorectal and pancreatic tumor cell lines, but not to prostate or squamous tumor cell lines.

TABLE 4

Hybridoma vs. Recombinant mouse 16C3
FACS data, binding to tumor lines

| Antibody Sample | % LS174T tumor cell binding (MFI) |
|---|---|
| Goat anti-Mouse IgG-FITC control | 1.63 (43) |
| Purified m16C3, from H12 hyb. 525, 2 ug | 43.11 (118) |
| Purified m16C3, from H12 hyb. 712, 2 ug | 43.56 (113) |
| Purified m16C3, from H12 hyb. 713, 2 ug | 37.79 (110) |
| Purified m16C3, from H12 hyb. 840, 2 ug | 35.72 (92) |
| Purified m16C3, from rec-CHO, 1019, 2 ug | 41.45 (112) |
| Purified m16C3, from rec-CHO, 1115, 2 ug | 42.51 (114) |
| Purified m16C3, from rec-CHO, 1220, 2 ug | 37.46 (110) |
|  | % AsPC-1 Cells Stained (mfi) |
| Goat anti-Mouse FITC control | 1.01 (8) |
| mouse 16C3-hybridoma control, 712, 1 ug | 89.50 (138) |
| mouse 16C3-hybridoma control, 713, 5 uL | 81.42 (34) |
| Rec-CHO m16C3 supe #1 | 82.66 (28) |
| Rec-CHO m16C3 supe #2 | 83.86 (27) |
| Rec-CHO m16C3 supe #3 | 79.50 (18) |
| Rec-CHO m16C3 supe #4 | 83.08 (25) |

Example 11. Immunohistochemical Staining of Human Tissues Using Recombinant Mouse 16C3 Antibody The specificity of antigen binding displayed by the 16C3 antibody was measured by immunohistochemical staining of various human tissue samples, both cancer and normal specimens. Tissue microarrays, paraffin-embedded tissues, and fresh frozen human tissue samples were stained with purified mouse 16C3 antibody (IgG1), at 5 ug/mL, then detected using a peroxidase-conjugated anti-mouse IgG secondary antibody. The intensity of staining is indicated using a 0-4 rating system, with 0 indicating no cross-reactivity and 4 indicating very high cross-reactivity to the antigen or high expression of the antigen in a given specimen. Both the hybridoma-derived 16C3 antibody and the recombinant 16C3 antibody were tested. The results are summarized in the Tables 5 and 6, below:

TABLE 5

Staining with mouse 16C3 purified from hybridoma cells.

| Human Tissue Sample | Number positive/ number stained | Staining intensity |
|---|---|---|
| Colon cancer | 17/18 | +3 to +4 |
| Colon cancer mets | 18/18 | +3 to +4 |
| Pancreas cancer | 28/33 | +1 to +3 |
| Various other cancer tissues | 8/18 | +1 to +3 |
| Normal colon, pancreas, and other tissues | 0/74 |  |

TABLE 6

Staining with recombinant mouse 16C3 purified from CHO cells.

| Human Tissue Sample | Number positive/number stained | Staining intensity |
|---|---|---|
| Colon cancer | 45/45 | +2 to +3 |
| Pancreas cancer | 24/30 | +1 to +3 |
| Various other cancer tissues | 116/191 | weak to +4 |
| Normal colon, pancreas, and other tissues | 22/50 | weak to +2 |

Considered collectively, these data demonstrate over 95% binding specificity to colon cancers ($^{80}/_{81}$), approximately 80-85% binding specificity to pancreas cancers ($^{52}/_{63}$), and 40-60% binding specificity to other types of cancer (predominantly adenocarcinomas). There was some cross-reactivity to a small subset of normal tissues, most notably lung and ovarian tissues, and the overall cross-reactivity was approximately 44% ($^{22}/_{50}$). Interestingly, all normal human tissues that cross-reacted to the 16C3 antibody were performed with the recombinant produced antibody, (no cross-reactivity to normal human tissues observed with the hybridoma-produced 16C3), suggesting that the cross-reactivity may be related to an artifact of the CHO cell production process rather than related to the antibody itself.

Example 12. Testing of Humanized Variants of 16C3

Five different designs for converting the murine 16C3 antibody to a humanized, therapeutically useful antibody are presented in FIG. 5 and FIG. 6. Recombinant humanized 16C3 expressed in 293T cells, co-transfection of five variants in matrix experiment. Supernatants from the transient transfection were normalized to 2 ng/mL then diluted to estimate affinity compared to purified recombinant mouse 16C3, then tested for antigen binding potential to AsPC-1 pancreatic tumor cells by FACS, and compared to the recombinant mouse 16C3 antibody. The data shown in Table 7 demonstrates that each of the five variants of heavy chain could fold properly with each of the four variant light chains to result in antigen binding activity. The binding of each combination of humanized heavy chain and light chain was comparable to the binding by the original mouse 16C3 antibody. The data show that humanizing the 16C3 immunoglobulin by any of five different methods did not alter the antigen-recognition site of the resulting antibody. The binding of each was titratable with the amount of antibody, with each combination demonstrating similar titration profiles.

TABLE 7

FACS data from recombinant humanized 16C3.

| Antibody Sample | % AsPC-1 tumor cell binding (MFI) |
|---|---|
| Goat anti-Mouse IgG-FITC control | 1.55 (70) |
| RECm16C3 cntl., 100 ng | 61.66 (228) |
| RECm16C3 cntl., 20 ng | 47.91 (69) |
| RECm16C3 cntl., 4 ng | 4.26 (52) |
| RECm16C3 cntl., 0.8 ng | 1.28 (615) |
| Rabbit anti-Human IgG-FITC control (Heavy chain/Light chain) | 2.05 (59) |
| Rh16C3 supe 8: VEN/VEN-100 uL | 68.14 (1090) |
| Rh16C3 supe 8: VEN/VEN-20 uL | 65.93 (240) |
| Rh16C3 supe 8: VEN/VEN-4 uL | 46.11 (65) |
| Rh16C3 supe 10: VEN/ABB-100 uL | 64.19 (549) |
| Rh16C3 supe 10: VEN/ABB-20 uL | 62.24 (122) |
| Rh16C3 supe 10: VEN/ABB-4 uL | 22.10 (52) |
| Rh16C3 supe 11: VEN/SDR-100 uL | 67.99 (808) |
| Rh16C3 supe 11: VEN/SDR-20 uL | 66.45 (191) |
| Rh16C3 supe 11: VEN/SDR-4 uL | 32.30 (57) |
| Rh16C3 supe 12: VEN/FRA-100 uL | 67.22 (674) |
| Rh16C3 supe 12: VEN/FRA-20 uL | 64.11 (143) |
| Rh16C3 supe 12: VEN/FRA-4 uL | 25.65 (51) |
| Rh16C3 supe 14: CDR/VEN-100 uL | 62.66 (568) |
| Rh16C3 supe 14: CDR/VEN-20 uL | 59.92 (112) |
| Rh16C3 supe 14: CDR/VEN-4 uL | 16.89 (49) |
| Rh16C3 supe 16: CDR/ABB-100 uL | 64.49 (254) |
| Rh16C3 supe 16: CDR/ABB-20 uL | 49.61 (73) |
| Rh16C3 supe 16: CDR/ABB-4 uL | 5.85 (70) |
| Rh16C3 supe 17: CDR/SDR-100 uL | 68.02 (376) |
| Rh16C3 supe 17: CDR/SDR-20 uL | 54.78 (89) |
| Rh16C3 supe 17: CDR/SDR-4 uL | 10.21 (53) |
| Rh16C3 supe 18: CDR/FRA-100 uL | 61.54 (557) |
| Rh16C3 supe 18: CDR/FRA-20 uL | 57.34 (98) |
| Rh16C3 supe 18: CDR/FRA-4 uL | 17.55 (51) |
| Rh16C3 supe 20: ABB/VEN-100 uL | 65.72 (374) |
| Rh16C3 supe 20: ABB/VEN-20 uL | 57.34 (89) |
| Rh16C3 supe 20: ABB/VEN-4 uL | 6.39 (54) |
| Rh16C3 supe 22: ABB/ABB-100 uL | 66.31 (318) |
| Rh16C3 supe 22: ABB/ABB-20 uL | 50.30 (78) |
| Rh16C3 supe 22: ABB/ABB-4 uL | 7.63 (50) |
| Rh16C3 supe 23: ABB/SDR-100 uL | 66.33 (293) |
| Rh16C3 supe 23: ABB/SDR-20 uL | 52.12 (75) |
| Rh16C3 supe 23: ABB/SDR-4 uL | 6.58 (59) |
| Rh16C3 supe 24: ABB/FRA-100 uL | 65.15 (403) |
| Rh16C3 supe 24: ABB/FRA-20 uL | 57.63 (98) |
| Rh16C3 supe 24: ABB/FRA-4 uL | 12.29 (50) |
| Rh16C3 supe 26: SDR/VEN-100 uL | 67.94 (495) |
| Rh16C3 supe 26: SDR/VEN-20 uL | 62.15 (140) |
| Rh16C3 supe 26: SDR/VEN-4 uL | 12.69 (59) |
| Rh16C3 supe 28: SDR/ABB-100 uL | 66.58 (314) |
| Rh16C3 supe 28: SDR/ABB-20 uL | 54.71 (87) |
| Rh16C3 supe 28: SDR/ABB-4 uL | 8.59 (51) |
| Rh16C3 supe 29: SDR/SDR-100 uL | 67.95 (503) |
| Rh16C3 supe 29: SDR/SDR-20 uL | 61.56 (114) |
| Rh16C3 supe 29: SDR/SDR-4 uL | 15.87 (56) |
| Rh16C3 supe 30: SDR/FRA-100 uL | 65.87 (702) |
| Rh16C3 supe 30: SDR/FRA-20 uL | 64.45 (156) |
| Rh16C3 supe 30: SDR/FRA-4 uL | 29.29 (53) |
| Rh16C3 supe 32: FRA/VEN-100 uL | 66.03 (585) |
| Rh16C3 supe 32: FRA/VEN-20 uL | 63.64 (147) |
| Rh16C3 supe 32: FRA/VEN-4 uL | 22.69 (52) |
| Rh16C3 supe 34: FRA/ABB-100 uL | 67.38 (395) |
| Rh16C3 supe 34: FRA/ABB-20 uL | 58.89 (99) |
| Rh16C3 supe 34: FRA/ABB-4 uL | 12.30 (51) |
| Rh16C3 supe 35: FRA/SDR-100 uL | 68.01 (465) |
| Rh16C3 supe 35: FRA/SDR-20 uL | 61.35 (114) |
| Rh16C3 supe 35: FRA/SDR-4 uL | 14.23 (59) |
| Rh16C3 supe 36: FRA/FRA-100 uL | 67.88 (432) |
| Rh16C3 supe 36: FRA/FRA-20 uL | 59.15 (99) |
| Rh16C3 supe 36: FRA/FRA-4 uL | 8.68 (53) |

Example 13. Optimization and Testing of Recombinant Humanized 16C3 Antibody

Additionally, in silico analysis tools are useful in predicting potential T-cell epitopes in a protein. Such algorithms are useful to design improved recombinant proteins with a decreased likelihood of immunogenicity in humans. To take advantage of this predictive technology, the five variant humanized 16C3 heavy chain and light chain genes were analyzed and shown to harbor one or more predicted T-cell epitopes that might possibly induce an immunogenic response in humans with certain HLA haplotypes. Such analysis may be done using software such as Epimer or EpiMatrix, in silico epitope-mapping tools, or by a commercial vendor, such as Antitope, Ltd. (Cambridge, UK). In an attempt to remove these T-cell epitopes to decrease possible immunogenicity of a potential therapeutic 16C3 antibody, specific point mutations were made to delete the T-cell epitopes and replace specific amino acids that would result in a fully functional, but less immunogenic, antibody molecule. The protein sequence of the optimized humanized 16C3 antibody is shown in FIG. 12, with the bolded amino acids indicating CDRs, and "/" indicating the leader peptide/mature N-terminus junction and the variable/constant domain junction.

The genes for the h16C3-Abb* antibody were made by mutagenesis of the existing variant genes to yield the desired DNA sequences. Then, the h16C3-Abb* heavy and light chain genes were cloned into a mammalian expression plasmid and transfected into CHO cells. The supernatants of several resulting clones were tested for binding to LS174T (colon) and CFPAC-1 (pancreas) tumor cells by FACS, with Rabbit anti-Human IgG-FITC as the control. The data presented in Table 8 demonstrates that the optimized, humanized 16C3 (H16C3) gene designs resulted in an antibody with very good antigen recognition activity. This particular h16C3-Abb* design represents an antibody with high binding activity with potentially low immunogenicity and/or toxicity as a therapeutic antibody for use in cancers that express the target antigen.

TABLE 8

Result of FACS experiment on humanized 16C3-Abb* transfection supernatants.

| Antibody Sample | % binding to LS174T cells (mfi) | % binding to CFPAC-1 cells (mfi) |
|---|---|---|
| Control | 3.49 (33) | 2.10 (20) |
| H16C3-Abb* supe 1 | 54.40 (374) | 98.62 (411) |
| H16C3-Abb* supe 2 | 51.10 (299) | 97.70 (299) |
| H16C3-Abb* supe 3 | 55.20 (402) | 98.60 (486) |
| H16C3-Abb* supe 4 | 53.75 (333) | 98.68 (371) |
| H16C3-Abb* supe 5 | 56.24 (407) | 99.14 (447) |

The ADCC activity of h16C3-Abb* was tested against pancreatic CFPAC-1 and AsPC-1 carcinoma lines as target cells. The melanoma cell line, SK-MEL, served as a tumor cell specificity control. ADCC was assayed using a conventional four hour $^{111}$In-release assay using normal human PBMC as effector cells, and the results are shown as the percent isotope release (% lysis) below. Compared to the negative control antibody UPC-10, the data indicate antibody-specific killing activity by the humanized 16C3 antibody. The killing activity appeared to be specific for pancreatic tumor lines since no lysis was observed against the melanoma negative control cells. These data show that the killing activity of an antibody could be engineered through humanization of the mouse 16C3 antibody. Compared to the mouse 16C3 antibody, the humanized 16C3 antibody demonstrated superior killing activity, most likely due to the human Fc region that could interact more efficiently than the mouse Fc region with human effector cells.

TABLE 9

ADCC assay with hl6C3-Abb* antibody.

| Tumor Target | Effector:Target Ratio | % Specific ADCC Activity (±SEM) h16C3-Abb* | % Specific ADCC Activity (±SEM) UPC-10 control |
|---|---|---|---|
| AsPC-1 (pancreas) | 100 | 32.2 ± 0.56 | 0.4 ± 0.38 |
|  | 50 | 18.4 ± 2.67 | −0.1 ± 0.54 |
|  | 25 | 14.4 ± 1.66 | 0.2 ± 0.36 |

TABLE 9-continued

ADCC assay with hl6C3-Abb* antibody.

| Tumor Target | Effector:Target Ratio | % Specific ADCC Activity (±SEM) h16C3-Abb* | % Specific ADCC Activity (±SEM) UPC-10 control |
|---|---|---|---|
| CFPAC-1 (pancreas) | 100 | 48.7 ± 3.22 | 1.9 ± 0.26 |
|  | 50 | 40.9 ± 4.11 | 2.6 ± 0.49 |
|  | 25 | 19.4 ± 2.07 | 2.1 ± 0.20 |
| SK-MEL (melanoma) | 100 | 0.1 ± 1.28 | −0.6 ± 0.18 |
|  | 50 | −1.2 ± 0.78 | −1.8 ± 0.34 |
|  | 25 | 0.1 ± 0.2 | −1.1 ± 0.83 |

$^{111}$In-labeled target cells, antibodies used at 5 µg/well, IL-2 activated human PBMC used as effector cells, 4 hour incubation at 37° C. before harvest.

Example 14. Characterization of the CPAA Recognized by 16C3

Several characteristics of the antigen to which the 16C3 antibody binds were examined in western blots using various treatments. The data in Table 10 demonstrate that the 16C3 antigen is present in some, but not all, cultured colorectal and pancreatic tumor cells. Importantly, the 16C3 antigen is present in fetal tissue extracts derived from the gut and intestine. The Fraction I positive specimens represent eluates (Fraction 1) from Sephadex G-200 column chromatography runs using embryonic tissues dissected and subjected to the Hollinshead method of membrane protein extraction and purification. The colorectal tumor specimens were obtained from surgical procedures. The tissues were minced and subjected to total protein extraction using detergents. Table 10 shows data from the expression of 16C3 tumor antigen in various tumor cells by western blot of these cell extracts. These data suggest that the 16C3 tumor antigen may be expressed during the embryonic stage of life as well as in cancer. The expression of the 16C3 antigen, therefore, could be developmentally regulated to be expressed during embryonic tissue development, and again during cancer development.

TABLE 10

Expression of 16C3 tumor antigen in various tumor cells.

| Cell Line | 16C3 Antigen |
|---|---|
| SW1116 (colorectal) | Positive (MW ~220 kDa) |
| SW480 (colorectal) | negative |
| SW1463 (colorectal) | negative |
| COLO-205 (colorectal) | Positive (MW ~220 kDa) |
| CALU-1 (lung) | negative |
| PANC-1 (pancreas) | negative |
| PR-22 (prostate) | negative |
| HT-29 (colorectal) | Positive (MW ~220 kDa and 110 kDa) |
| LS174T (colorectal) | Positive (MW ~220 kDa and 110 kDa minor |
| CFPAC-1 (pancreas) | Positive (MW ~220 kDa and 110 kDa) |
| ASPC-1 (pancreas) | Positive (MW ~220 kDa and 110 kDa) |
| Human Tissue Preparation | |
| Fetal gut, Fraction I, Dec. 20, 1972 | Positive (MW ~220 kDa and 110 kDa) |
| Fetal intestine, Fraction I, Jun. 24, 1975 | Positive (MW ~220 kDa and 110 kDa) |
| Colorectal tumor tissues, resected | Positive (MW ~220 kDa and 110 kDa) |

Figure 8:
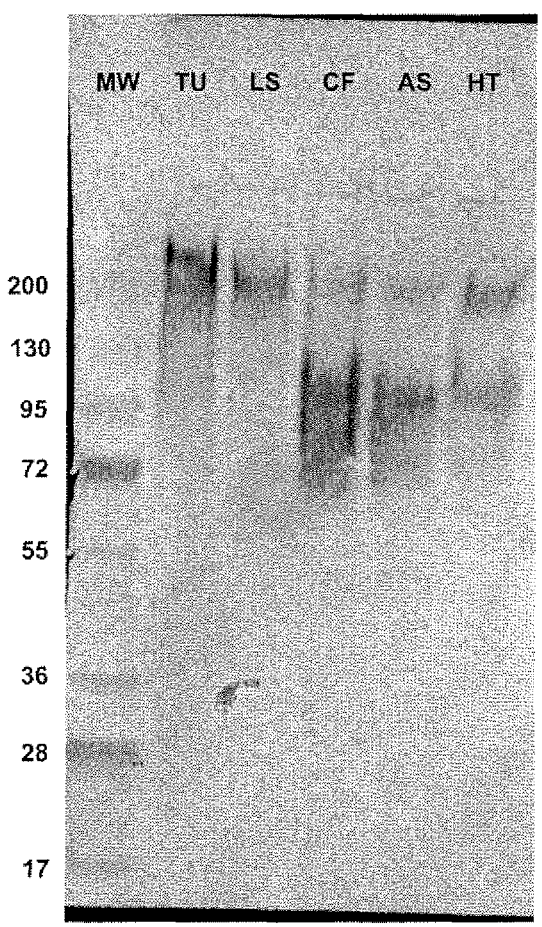
FIG. 8 is a radiograph of a western blot analysis of various cell lines using 16C3 antibody against the untreated 16C3 tumor antigen. TU=patient resected tumor sample (colorectal); LS=LS174; CF=CFPAC-1; AS=ASPC-1; HT=HT29.
Figure 9:
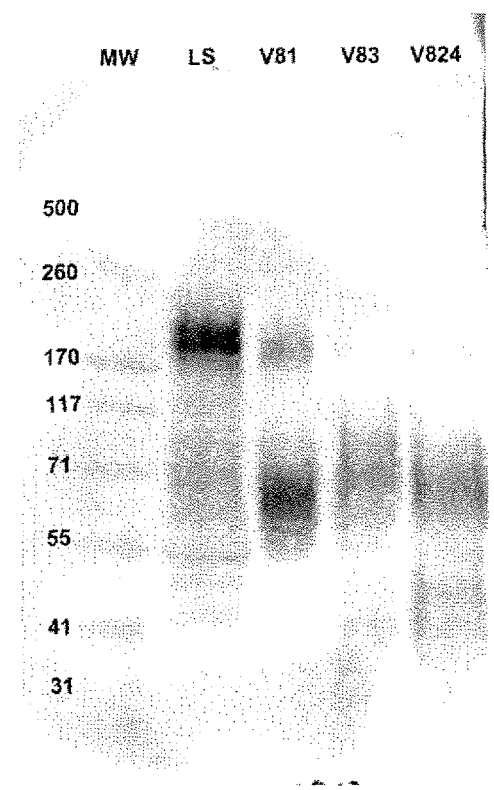
FIG. 9 is a radiograph of a western blot representing the protease VS-treated 16C3 tumor antigen. Protease V8 treatment of 16C3 antigen from LS174 cell line and detection of the antigen using Western blot. LS=untreated antigen; V81=incubation with protease V8 for 1 hour at room temperature (RT); V83=incubation with protease V8 for 3 hours at RT; V824=incubation with protease V8 for 24 hour at RT.
Figure 10:
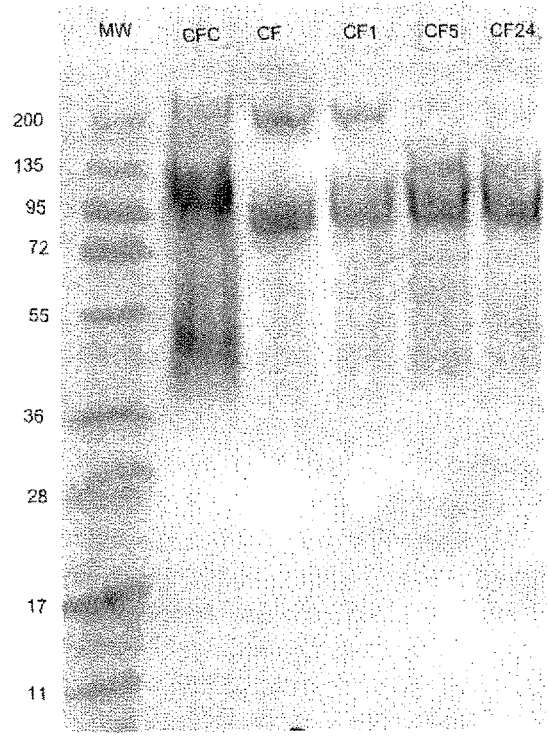
FIG. 10 shows a western blot representing the PNGase-F treated 16C3 tumor antigen, 16C3 antigen from CFPAC-1 was treated with PNGase-F (removes N-linked glycosylation) for various times. CFC=antigen incubated 24 hours at RT without enzyme; CF=control antigen untreated; CF1=antigen treated with enzyme 1 hour at RT; CF5=antigen treated with enzyme for 5 hours; CF24=antigen treated with enzyme for 24 hours. The high molecular weight band is affected, but the low molecular weight band is not affected.

A qualitative description of the 16C3 tumor antigen expressed by colorectal and pancreatic tumor cell lines was pursued using western blot analysis following various chemical treatments. These findings are presented in FIG. 8-FIG. 11, and Table 11.

TABLE 11

Western blot analysis following various chemical treatments.

| | Tumor Cell Line | | |
|---|---|---|---|
| Characteristic | LS174T | CFPAC | ASPC-1 |
| Semi quantitation of antigen expression in supernatant (LS174 is expressed as 100%) | By western blot Relative amount 100% | By western blot Relative amount 300% | By western blot Relative amount ~30% |
| Semi quantitation of antigen expression in cell pellet (LS174 is expressed as 100%) | By western blot Relative amount 100% | By western blot Relative amount 200% | By western blot Relative amount 80% |
| Ratio of presence in cell pellet vs. supernatant | 100/20 | 100/20 | 100/20 |
| ~MW in SDS gel as determined by western blot | ~200 kDa and 110 kDa (minor component) | ~200 kDa and 110 kDa | ~200 kDa and 110 kDa |
| Effect of reducing agents DDT or 2-ME | No effect on antigenicity or molecular weight | No effect on antigenicity or molecular weight | No effect on antigenicity or molecular weight |
| Glycosidase treatment | Antigenicity is not effected by glycosidase treatment, but PNGase F reduced the molecular weight of the 200 kDa band to ~130 kDa. The lower (110 kDa) band is not effected by PNGase F | | |
| Beta elimination using NaOH | Loss of antigenicity | | |
| Trypsin treatment for 24 hours at 25° C. or 37° C. | Antigenicity not effected but reduction of the molecular weight (diffuse broad band) | | Not Done |
| Protease V8 treatment 24 hours at 25° c. | Antigenicity not effected but reduction of the molecular weight (diffuse broad band) | | Not done |

Although this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

We claim:

1. An isolated 16C3 colorectal and pancreatic carcinoma-associated antigen (16C3 CPAA) antibody or antigen-binding fragment thereof comprising (a) a light chain comprising a CDR1 comprising the amino acid sequence of SEQ ID NO: 1 or SEQ ID NO: 4, a CDR2 comprising the amino acid sequence of SEQ ID NO: 2 or SEQ ID NO: 5, and a CDR3 comprising the amino acid sequence of SEQ ID NO: 3 or SEQ ID NO: 6; and (b) a heavy chain comprising a CDR1 comprising the amino acid sequence of SEQ ID NO: 7, a CDR2 comprising the amino acid sequence of SEQ ID NO: 8 or SEQ ID NO: 10 and a CDR3 comprising the amino acid sequence of SEQ ID NO: 9 or SEQ ID NO: 11.

2. The isolated antibody or antigen-binding fragment thereof of claim 1, wherein said antibody is conjugated to or is comprised in association with a cytotoxic agent.

3. The isolated antibody or antigen-binding fragment thereof of claim 2, wherein said cytotoxic agent comprises a moiety that inhibits DNA synthesis, a moiety that inhibits RNA synthesis, a moiety that inhibits protein synthesis, a radionuclide, chemotherapeutic drug, cytotoxic protein, a ribosomal inhibiting protein, $^{212}$Bi, $^{131}$I, $^{188}$Re, $^{90}$Y, vindesine, methotrexate, adriamycin, cisplatin, pokeweed antiviral protein, *Pseudomonas* exotoxin A, ricin, *diphtheria* toxin, ricin A chain, a phospholipase enzyme, daunorubicin, doxorubicin, methotrexate, or Mitomycin C.

4. The isolated antibody or antigen-binding fragment thereof of claim 1, wherein said antibody is conjugated to a label.

5. The isolated antibody or antigen-binding fragment thereof of claim 4, wherein said label comprises a chemiluminescent agent, fluorescence-emitting metal, enzyme, enzyme cofactor, enzyme inhibitor, fluorescent agent, bioluminescent agent, or a radioactive label.

6. The isolated antibody or antigen-binding fragment thereof of claim 1, wherein said antibody or antigen-binding fragment thereof binds the 16C3 colorectal and pancreatic carcinoma-associated antigen (16C3 CPAA).

7. The isolated antibody or antigen-binding fragment thereof of claim 1, wherein said antibody is an Fab, Fab', F(ab')2, Fv, CDR, paratope, or a portion of an antibody that is capable of binding the antigen.

8. The isolated antibody or antigen-binding fragment thereof of claim 1, wherein said antibody is chimeric, humanized, anti-idiotypic, or bifunctional antibody.

9. The isolated antibody or antigen-binding fragment thereof of claim 1, wherein the antibody has anti-tumor activity.

10. The isolated antibody or antigen-binding fragment thereof of claim 1, wherein said antibody comprises a human IgG1 constant region.

11. The isolated antibody or antigen-binding fragment thereof of claim 1, wherein said human IgG1 constant region comprises a gamma-1 constant region.

12. The isolated antibody or antigen-binding fragment thereof of claim 1, wherein said human IgG1 constant region comprises a kappa-1 constant region.

13. A composition comprising the antibody of claim 1 and a carrier.

14. The isolated antibody or antigen-binding fragment thereof of claim 1, wherein said antibody light chain comprises the amino acid sequence of SEQ ID NO: 12, 14, 16, 17, 18, 19, 20, 21, 29, or a humanized variant thereof.

15. The isolated antibody or antigen-binding fragment thereof of claim 1, wherein said antibody heavy chain comprises the amino acid sequence of SEQ ID NO: 13, 15, 22, 23, 24, 27, 28, or a humanized variant thereof.

16. The isolated antibody or antigen-binding fragment thereof of claim 1, wherein said antibody or antigen-binding fragment thereof is chimeric.

17. The isolated antibody or antigen-binding fragment thereof of claim 1, wherein said antibody or antigen-binding fragment thereof is humanized.

18. The isolated antibody or antigen-binding fragment thereof of claim 1, wherein said antibody or antigen-binding fragment thereof is an Fab, Fab', F(ab')2, or Fv fragment of an antibody.

19. A composition comprising the antibody of claim 1 fixed to a solid phase support.

20. The composition of claim 19, wherein said solid support comprises a bead, test tube, sheet, culture dish, or test strip.

\* \* \* \* \*

```
                        SEQUENCE LISTING

<160> NUMBER OF SEQ ID NOS: 30

<210> SEQ ID NO 1
<211> LENGTH: 11
<212> TYPE: PRT
<213> ORGANISM: Mus musculus

<400> SEQUENCE: 1

Gly Ala Ser Glu Asn Ile Tyr Gly Ala Leu Asn
1               5                   10

<210> SEQ ID NO 2
<211> LENGTH: 7
<212> TYPE: PRT
<213> ORGANISM: Mus musculus

<400> SEQUENCE: 2

Gly Ala Ser Asn Leu Ala Asp
1               5

<210> SEQ ID NO 3
<211> LENGTH: 9
<212> TYPE: PRT
<213> ORGANISM: Mus musculus

<400> SEQUENCE: 3

Gln Asn Val Leu Ser Ser Pro Tyr Thr
1               5
```

```
<210> SEQ ID NO 4
<211> LENGTH: 11
<212> TYPE: PRT
<213> ORGANISM: Homo sapiens

<400> SEQUENCE: 4

Gln Ala Ser Glu Asn Ile Tyr Gly Ala Leu Asn
1               5                   10

<210> SEQ ID NO 5
<211> LENGTH: 7
<212> TYPE: PRT
<213> ORGANISM: Homo sapiens

<400> SEQUENCE: 5

Gly Ala Ser Asn Leu Ala Thr
1               5

<210> SEQ ID NO 6
<211> LENGTH: 9
<212> TYPE: PRT
<213> ORGANISM: Homo sapiens

<400> SEQUENCE: 6

Gln Gln Val Leu Ser Ser Pro Tyr Thr
1               5

<210> SEQ ID NO 7
<211> LENGTH: 10
<212> TYPE: PRT
<213> ORGANISM: Mus musculus

<400> SEQUENCE: 7

Gly Tyr Thr Phe Thr Asp Tyr Ala Met His
1               5                   10

<210> SEQ ID NO 8
<211> LENGTH: 17
<212> TYPE: PRT
<213> ORGANISM: Mus musculus

<400> SEQUENCE: 8

Leu Ile Ser Thr Tyr Ser Gly Asp Thr Lys Tyr Asn Gln Asn Phe Lys
1               5                   10                  15

Gly

<210> SEQ ID NO 9
<211> LENGTH: 12
<212> TYPE: PRT
<213> ORGANISM: Mus musculus

<400> SEQUENCE: 9

Gly Asp Tyr Ser Gly Ser Arg Tyr Trp Phe Ala Tyr
1               5                   10

<210> SEQ ID NO 10
<211> LENGTH: 17
<212> TYPE: PRT
<213> ORGANISM: Homo sapiens

<400> SEQUENCE: 10

Leu Ile Ser Thr Tyr Ser Gly Asp Thr Lys Tyr Asn Gln Asn Phe Gln
1               5                   10                  15

Gly
```

<210> SEQ ID NO 11
<211> LENGTH: 12
<212> TYPE: PRT
<213> ORGANISM: Homo sapiens

<400> SEQUENCE: 11

Gly Asp Tyr Ser Gly Ser Arg Tyr Trp Phe Ala Tyr
1               5                   10

<210> SEQ ID NO 12
<211> LENGTH: 965
<212> TYPE: DNA
<213> ORGANISM: Mus musculus

<400> SEQUENCE: 12

| | |
|---|---|
| gcggggcagc ctcacacaga acacacacag atatgggtgt acccactcag ctcctgttgc | 60 |
| tgtggcttac agtcgtagtt gtcagatgtg acatccagat gactcagtct ccagcttcac | 120 |
| tgtctgcatc tgtgggagaa actgtcacca tcacatgtgg agcaagtgag aatatttacg | 180 |
| gtgctttaaa ttggtatcag cggaaacagg gaaaatctcc tcagctcctg atttatggcg | 240 |
| caagtaattt ggcagatggc atgtcatcga ggttcagtgg cagtggatct ggtagacagt | 300 |
| attctctcaa gatcagtagc ctgcatcctg acgatgttgc aacgtattac tgtcaaaatg | 360 |
| tattaagtag tccgtacacg ttcggagggg gaccaagct ggaaataaaa cgggctgatg | 420 |
| ctgcaccaac tgtatccatc ttcccaccat ccagtgagca gttaacatct ggaggtgcct | 480 |
| cagtcgtgtg cttcttgaac aacttctacc ccaaagacat caatgtcaag tggaagattg | 540 |
| atggcagtga acgacaaaat ggcgtcctga cagttggac tgatcaggac agcaaagaca | 600 |
| gcacctacag catgagcagc accctcacgt tgaccaagga cgagtatgaa cgacataaca | 660 |
| gctatacctg tgaggccact cacaagacac aacttcacc cattgtcaag agcttcaaca | 720 |
| ggaatgagtg ttagagacaa aggtcctgag acgccaccac cagctcccca gctccatcct | 780 |
| atcttcccctt ctaaggtctt ggaggcttcc ccacaagcga cctaccactg ttgcggtgct | 840 |
| ccaaacctcc tccccacctc cttctcctcc tcctcccttt ccttggcttt tatcatgcta | 900 |
| atatttgcag aaaatattca ataaagtgag tctttgcaca aaaaaaaaaa aaaaaaaaa | 960 |
| aaaaa | 965 |

<210> SEQ ID NO 13
<211> LENGTH: 1575
<212> TYPE: DNA
<213> ORGANISM: Mus musculus

<400> SEQUENCE: 13

| | |
|---|---|
| acgcgggaca cagtagtctc tacagtcaca ggagtacaca ggacattgcc atgggttgga | 60 |
| gctgtatcat cttcttttctg gtagcaacag ctacaggtgt gcactcccag gtccagctgc | 120 |
| agcagtctgg gcctgaggtg gtgaggcctg gggtctcagt gaagatttcc tgcaagggtt | 180 |
| ccggctacac attcactgat tatgctatgc actgggtgaa gcagagtcat gcaaagagtc | 240 |
| tcgagtggat tggacttatt agtacttaca gtggtgatac aaagtacaac cagaacttta | 300 |
| agggcaaggc cacaatgact gtagacaaat cctccaacac agcctatatg aacttgcca | 360 |
| gattgacatc tgaggattct gccatctatt actgtgcaag aggggattat tccggtagta | 420 |
| ggtactggtt tgcttactgg ggccaaggga ctctggtcac tgtctctgca gccaaaacga | 480 |
| cacccccatc tgtctatcca ctggcccctg gatctgctgc ccaaactaac tccatggtga | 540 |

-continued

```
ccctgggatg cctggtcaag ggctatttcc ctgagccagt gacagtgacc tggaactctg      600
gatccctgtc cagcggtgtg cacaccttcc cagctgtcct gcagtctgac ctctacactc      660
tgagcagctc agtgactgtc ccctccagca cctggcccag cgagaccgtc acctgcaacg      720
ttgcccaccc ggccagcagc accaaggtgg acaagaaaat tgtgcccagg gattgtggtt      780
gtaagccttg catatgtaca gtcccagaag tatcatctgt cttcatcttc cccccaaagc      840
ccaaggatgt gctcaccatt actctgactc taaggtcac gtgtgttgtg gtagacatca       900
gcaaggatga tcccgaggtc cagttcagct ggtttgtaga tgatgtggag gtgcacacag      960
ctcagacgca accccgggag gagcagttca acagcacttt ccgctcagtc agtgaacttc     1020
ccatcatgca ccaggactgg ctcaatggca aggagttcaa atgcagggtc aacagtgcag     1080 cttttccctgc ccccatcgag aaaccatct ccaaaaccaa aggcagaccg aaggctccac     1140
aggtgtacac cattccacct cccaaggagc agatggccaa ggataaagtc agtctgacct     1200
gcatgataac agacttcttc cctgaagaca ttactgtgga gtggcagtgg aatgggcagc     1260
cagcggagaa ctacaagaac actcagccca tcatggacac agatggctct tacttcgtct     1320
acagcaagct caatgtgcag aagagcaact gggaggcagg aaatactttc acctgctctg     1380
tgttacatga gggcctgcac aaccaccata ctgagaagag cctctcccac tctcctggta     1440
aatgatccca gtgtccttgg agccctctgg ccctacagga ctttgacacc tacctccacc     1500
cctccctgta aaataaagc acccagcact gcctcgggac cctgcataaa aaaaaaaaaa      1560
aaaaaaaaaa aaaaa                                                     1575
```

<210> SEQ ID NO 14
<211> LENGTH: 107
<212> TYPE: PRT
<213> ORGANISM: Mus musculus

<400> SEQUENCE: 14

Leu Met Thr Gln Ser Pro Ala Ser Leu Ser Ala Ser Val Gly Glu Thr
1               5                   10                  15

Val Thr Ile Thr Cys Gly Ala Ser Glu Asn Ile Tyr Gly Ala Leu Asn
            20                  25                  30

Trp Tyr Gln Arg Lys Gln Gly Lys Ser Pro Gln Leu Leu Ile Tyr Gly
        35                  40                  45

Ala Ser Asn Leu Ala Asp Gly Met Ser Ser Arg Phe Ser Gly Ser Gly
    50                  55                  60

Ser Gly Arg Gln Tyr Ser Leu Lys Ile Ser Ser Leu His Pro Asp Asp
65                  70                  75                  80

Val Ala Thr Tyr Tyr Cys Gln Asn Val Leu Ser Ser Pro Tyr Thr Phe
                85                  90                  95

Gly Gly Gly Thr Lys Leu Glu Ile Lys Lys Gly
            100                 105

<210> SEQ ID NO 15
<211> LENGTH: 116
<212> TYPE: PRT
<213> ORGANISM: Mus musculus

<400> SEQUENCE: 15

Leu Glu Glu Ser Gly Pro Glu Val Val Arg Pro Gly Val Ser Val Lys
1               5                   10                  15

Ile Ser Cys Lys Gly Ser Gly Tyr Thr Phe Thr Asp Tyr Ala Met His
            20                  25                  30

-continued

```
Trp Val Lys Gln Ser His Ala Lys Ser Leu Glu Trp Ile Gly Leu Ile
         35                  40                  45

Ser Thr Tyr Ser Gly Asp Thr Lys Tyr Asn Gln Asn Phe Lys Gly Lys
 50                  55                  60

Ala Thr Met Thr Val Asp Lys Ser Ser Asn Thr Ala Tyr Met Glu Leu
 65                  70                  75                  80

Ala Arg Leu Thr Ser Glu Asp Ser Ala Ile Tyr Tyr Cys Ala Arg Gly
                 85                  90                  95

Asp Tyr Ser Gly Ser Arg Tyr Trp Phe Ala Tyr Trp Gly Gln Gly Thr
                100                 105                 110

Thr Val Thr Arg
        115

<210> SEQ ID NO 16
<211> LENGTH: 107
<212> TYPE: PRT
<213> ORGANISM: Mus musculus

<400> SEQUENCE: 16

Asp Ile Gln Met Thr Gln Ser Pro Ala Ser Leu Ser Ala Ser Val Gly
 1               5                  10                  15

Glu Thr Val Thr Ile Thr Cys Gly Ala Ser Glu Asn Ile Tyr Gly Ala
                 20                  25                  30

Leu Asn Trp Tyr Gln Arg Lys Gln Gly Lys Ser Pro Gln Leu Leu Ile
         35                  40                  45

Tyr Gly Ala Ser Asn Leu Ala Asp Gly Met Ser Ser Arg Phe Ser Gly
 50                  55                  60

Ser Gly Ser Gly Arg Gln Tyr Ser Leu Lys Ile Ser Ser Leu His Pro
 65                  70                  75                  80

Asp Asp Val Ala Thr Tyr Tyr Cys Gln Asn Val Leu Ser Ser Pro Tyr
                 85                  90                  95

Thr Phe Gly Gly Gly Thr Lys Leu Glu Ile Lys
                100                 105

<210> SEQ ID NO 17
<211> LENGTH: 107
<212> TYPE: PRT
<213> ORGANISM: Artificial Sequence
<220> FEATURE:
<223> OTHER INFORMATION: Description of artificial sequence: chimeric
      (or humanized) mAb sequence, from Mus musculus and Homo sapiens

<400> SEQUENCE: 17

Asp Ile Gln Met Thr Gln Ser Pro Ser Ser Leu Ser Ala Ser Val Gly
 1               5                  10                  15

Asp Arg Val Thr Ile Thr Cys Gly Ala Ser Glu Asn Ile Tyr Gly Ala
                 20                  25                  30

Leu Asn Trp Tyr Gln Arg Lys Pro Gly Lys Ser Pro Lys Leu Leu Ile
         35                  40                  45

Tyr Gly Ala Ser Asn Leu Ala Asp Gly Met Pro Ser Arg Phe Ser Gly
 50                  55                  60

Ser Gly Ser Gly Arg Gln Tyr Thr Leu Thr Ile Ser Ser Leu Gln Pro
 65                  70                  75                  80

Glu Asp Val Ala Thr Tyr Tyr Cys Gln Asn Val Leu Ser Ser Pro Tyr
                 85                  90                  95

Thr Phe Gly Gly Gly Thr Lys Leu Glu Ile Lys
                100                 105
```

```
<210> SEQ ID NO 18
<211> LENGTH: 107
<212> TYPE: PRT
<213> ORGANISM: Artificial Sequence
<220> FEATURE:
<223> OTHER INFORMATION: Description of artificial sequence: chimeric
      (or humanized) mAb sequence, from Mus musculus and Homo sapiens

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 19
<211> LENGTH: 107
<212> TYPE: PRT
<213> ORGANISM: Artificial sequence
<220> FEATURE:
<223> OTHER INFORMATION: Description of artificial sequence: chimeric
      (or humanized) mAb sequence, from Mus musculus and Homo sapiens

<400> SEQUENCE: 19

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105

<210> SEQ ID NO 20
<211> LENGTH: 107
<212> TYPE: PRT
<213> ORGANISM: Artificial sequence
<220> FEATURE:
<223> OTHER INFORMATION: Description of artificial sequence: chimeric
      (or humanized) mAb sequence, from Mus musculus and Homo sapiens

<400> SEQUENCE: 20

Asp Ile Gln Met Thr Gln Ser Pro Ser Ser Leu Ser Ala Ser Val Gly
1               5                   10                  15
```

```
Asp Arg Val Thr Ile Thr Cys Gln Ala Ser Glu Asn Ile Tyr Gly Ala
            20                  25                  30

Leu Asn Trp Tyr Gln Arg Lys Pro Gly Lys Ser Pro Lys Leu Leu Ile
        35                  40                  45

Tyr Gly Ala Ser Asn Leu Ala Thr Gly Met Pro Ser Arg Phe Ser Gly
    50                  55                  60

Ser Gly Ser Gly Arg Gln Tyr Thr Phe Thr Ile Ser Ser Leu Gln Pro
65                  70                  75                  80

Glu Asp Ile Ala Thr Tyr Tyr Cys Gln Gln Val Leu Ser Ser Pro Tyr
                85                  90                  95

Thr Phe Gly Gly Gly Thr Lys Leu Glu Ile Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Description of artificial sequence: chimeric
      (or humanized) mAb sequence, from Mus musculus and Homo sapiens

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Arg Lys Pro Gly Lys Ser Pro Asn Leu Leu Ile
        35                  40                  45

Tyr Gly Ala Ser Asn Leu Ala Asp Gly Met Pro Ser Arg Phe Ser Gly
    50                  55                  60

Ser Gly Ser Gly Arg Gln Tyr Thr Leu Thr Ile Ser Ser Leu Gln Pro
65                  70                  75                  80

Glu Asp Val Ala Thr Tyr Tyr Cys Gln Asn Val Leu Ser Ser Pro Tyr
                85                  90                  95

Thr Phe Gly Gly Gly Thr Lys Leu Glu Ile Lys
            100                 105
```

<210> SEQ ID NO 22
<211> LENGTH: 121
<212> TYPE: PRT
<213> ORGANISM: Mus musculus

<400> SEQUENCE: 22

```
Gln Val Gln Leu Gln Gln Ser Gly Pro Glu Val Val Arg Pro Gly Val
1               5                   10                  15

Ser Val Lys Ile Ser Cys Lys Gly Ser Gly Tyr Thr Phe Thr Asp Tyr
            20                  25                  30

Ala Met His Trp Val Lys Gln Ser His Ala Lys Ser Leu Glu Trp Ile
        35                  40                  45

Gly Leu Ile Ser Thr Tyr Ser Gly Asp Thr Lys Tyr Asn Gln Asn Phe
    50                  55                  60

Lys Gly Lys Ala Thr Met Thr Val Asp Lys Ser Ser Asn Thr Ala Tyr
65                  70                  75                  80

Met Glu Leu Ala Arg Leu Thr Ser Glu Asp Ser Ala Ile Tyr Tyr Cys
                85                  90                  95

Ala Arg Gly Asp Tyr Ser Gly Ser Arg Tyr Trp Phe Ala Tyr Trp Gly
            100                 105                 110
```

Gln Gly Thr Leu Val Thr Val Ser Ala
        115                 120

<210> SEQ ID NO 23
<211> LENGTH: 121
<212> TYPE: PRT
<213> ORGANISM: Artificial sequence
<220> FEATURE:
<223> OTHER INFORMATION: Description of artificial sequence: chimeric
      (or humanized) mAb sequence, from Mus musculus and Homo sapiens

<400> SEQUENCE: 23

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Arg Leu Glu Trp Ile
        35                  40                  45

Gly Leu Ile Ser Thr Tyr Ser Gly Asp Thr Lys Tyr Asn Gln Asn Phe
50                  55                  60

Lys Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 24
<211> LENGTH: 121
<212> TYPE: PRT
<213> ORGANISM: Artificial sequence
<220> FEATURE:
<223> OTHER INFORMATION: Description of artificial sequence: chimeric
      (or humanized) mAb sequence, from Mus musculus and Homo sapiens

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Leu Ile Ser Thr Tyr Ser Gly Asp Thr Lys Tyr Asn Gln Asn Phe
50                  55                  60

Lys Gly Lys Ala Thr Met Thr Val Asp Thr Ser Ile Ser Thr Ala Tyr
65                  70                  75                  80

Met Glu Leu Ser Arg Leu Arg Ser Asp Asp Thr Ala Ile Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120

<210> SEQ ID NO 25
<211> LENGTH: 121
<212> TYPE: PRT
<213> ORGANISM: Artificial sequence
<220> FEATURE:

<223> OTHER INFORMATION: Description of artificial sequence: chimeric
(or humanized) mAb sequence, from Mus musculus and Homo sapiens

<400> SEQUENCE: 25

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Arg Leu Glu Trp Met
        35                  40                  45

Gly Leu Ile Ser Thr Tyr Ser Gly Asp Thr Lys Tyr Ser Gln Lys Phe
    50                  55                  60

Gln Gly Arg Val Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120
```

<210> SEQ ID NO 26
<211> LENGTH: 121
<212> TYPE: PRT
<213> ORGANISM: Artificial sequence
<220> FEATURE:
<223> OTHER INFORMATION: Description of artificial sequence: chimeric
(or humanized) mAb sequence, from Mus musculus and Homo sapiens

<400> SEQUENCE: 26

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Arg Leu Glu Trp Ile
        35                  40                  45

Gly Leu Ile Ser Thr Tyr Ser Gly Asp Thr Lys Tyr Asn Gln Lys Phe
    50                  55                  60

Gln Gly Lys Ala Thr Met Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asp Tyr Ser Gly Ser Arg Tyr Trp Phe Ala Tyr Trp Gly
            100                 105                 110

Gln Gly Thr Leu Val Thr Val Ser Ser
        115                 120
```

<210> SEQ ID NO 27
<211> LENGTH: 121
<212> TYPE: PRT
<213> ORGANISM: Artificial sequence
<220> FEATURE:
<223> OTHER INFORMATION: Description of artificial sequence: chimeric
(or humanized) mAb sequence, from Mus musculus and Homo sapiens

<400> SEQUENCE: 27

```
Gln Val Gln Leu Val Gln Ser Gly Ala Glu Val Lys Lys Pro Gly Ala
1               5                   10                  15

Ser Val Lys Val Ser Cys Lys Gly Ser Gly Tyr Thr Phe Thr Asp Tyr
```

```
                  20                  25                  30
Ala Met His Trp Val Arg Gln Val His Ala Gln Gly Leu Glu Trp Ile
            35                  40                  45
Gly Leu Ile Ser Thr Tyr Ser Gly Asp Thr Lys Tyr Asn Gln Asn Phe
        50                  55                  60
Lys Gly Lys Ala Thr Met Thr Val Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Gly Asp Tyr Ser Gly Ser Arg Tyr Trp Phe Ala Tyr Trp Gly
            100                 105                 110
Gln Gly Thr Leu Val Thr Val Ser Ser
            115                 120
```

<210> SEQ ID NO 28
<211> LENGTH: 470
<212> TYPE: PRT
<213> ORGANISM: Artificial sequence
<220> FEATURE:
<223> OTHER INFORMATION: Description of artificial sequence: optimized
      humanized mAb sequence, from Homo sapiens

<400> SEQUENCE: 28

```
Met Gly Trp Ser Cys Ile Ile Phe Phe Leu Val Ala Thr Ala Thr Gly
1               5                   10                  15
Val His Ser Gln Val Gln Leu Val Gln Ser Gly Ala Glu Val Lys Lys
            20                  25                  30
Pro Gly Ala Ser Val Lys Val Ser Cys Lys Ala Ser Gly Tyr Thr Phe
        35                  40                  45
Thr Asp Tyr Ala Met His Trp Val Arg Gln Ala Pro Gly Gln Arg Leu
    50                  55                  60
Glu Trp Met Gly Leu Ile Ser Thr Tyr Ser Gly Asp Thr Lys Tyr Asn
65                  70                  75                  80
Gln Asn Phe Gln Gly Arg Val Thr Met Thr Val Asp Lys Ser Ala Ser
                85                  90                  95
Thr Ala Tyr Met Glu Leu Ser Ser Leu Arg Ser Glu Asp Thr Ala Val
            100                 105                 110
Tyr Tyr Cys Ala Arg Gly Asp Tyr Ser Gly Ser Arg Tyr Trp Phe Ala
        115                 120                 125
Tyr Trp Gly Gln Gly Thr Leu Val Thr Val Ser Ser Ala Ser Thr Lys
    130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Ser Leu Gly Thr Gln Thr Tyr Ile Cys Asn
    210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
```

```
Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 29
<211> LENGTH: 233
<212> TYPE: PRT
<213> ORGANISM: Artificial sequence
<220> FEATURE:
<223> OTHER INFORMATION: Description of artificial sequence: optimized
      humanized mAb sequence, from Homo sapiens

<400> SEQUENCE: 29

Met Gly Val Pro Thr Gln Leu Leu Leu Trp Leu Thr Val Val
1               5                   10                  15

Val Arg Cys Asp Ile Gln Met Thr Gln Ser Pro Ser Ser Leu Ser Ala
                20                  25                  30

Ser Val Gly Asp Arg Val Thr Ile Thr Cys Gln Ala Ser Glu Asn Ile
            35                  40                  45

Tyr Gly Ala Leu Asn Trp Tyr Gln Arg Lys Pro Gly Lys Ser Pro Lys
        50                  55                  60

Leu Leu Ile Tyr Gly Ala Ser Asn Leu Ala Thr Gly Met Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln Gln Val Leu Ser
            100                 105                 110

Ser Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140
```

```
Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165             170                 175

Asn Ser Gln Glu Ser Val Thr Glu Gln Asp Ser Lys Asp Ser Thr Tyr
            180             185                 190

Ser Leu Ser Ser Thr Leu Thr Leu Ser Lys Ala Asp Tyr Glu Lys His
        195             200                 205

Lys Val Tyr Ala Cys Glu Val Thr His Gln Gly Leu Ser Ser Pro Val
        210             215                 220

Thr Lys Ser Phe Asn Arg Gly Glu Cys
225                 230

<210> SEQ ID NO 30
<211> LENGTH: 17
<212> TYPE: PRT
<213> ORGANISM: Homo sapiens

<400> SEQUENCE: 30

Leu Ile Ser Thr Tyr Ser Gly Asp Thr Lys Tyr Ser Gln Lys Phe Gln
1               5                   10                  15

Gly
```